US008262733B2

(12) United States Patent
Beger et al.

(10) Patent No.: US 8,262,733 B2
(45) Date of Patent: Sep. 11, 2012

(54) INTERVERTEBRAL DISK PROSTHESIS SYSTEM

(75) Inventors: Jens Beger, Tuttlingen (DE); Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 455 days.

(21) Appl. No.: 12/497,132

(22) Filed: Jul. 2, 2009

(65) Prior Publication Data
US 2010/0004749 A1    Jan. 7, 2010

(30) Foreign Application Priority Data
Jul. 3, 2008  (DE) .................. 10 2008 032 691

(51) Int. Cl.
A61F 2/44  (2006.01)
(52) U.S. Cl. ............... 623/17.14; 623/17.11; 623/17.13; 623/17.15; 623/17.16
(58) Field of Classification Search ............... 623/17.11, 623/17.14, 17.15, 17.16
See application file for complete search history.

(56) References Cited

U.S. PATENT DOCUMENTS

| 5,782,832 | A  | * | 7/1998  | Larsen et al. | 623/17.11 |
| 5,895,428 | A  | * | 4/1999  | Berry | 623/17.15 |
| 6,733,532 | B1 | * | 5/2004  | Gauchet et al. | 623/17.12 |
| 7,217,291 | B2 |   | 5/2007  | Zucherman et al. |  |
| 7,503,935 | B2 | * | 3/2009  | Zucherman et al. | 623/17.15 |
| 7,537,615 | B2 | * | 5/2009  | Lemaire | 623/17.15 |
| 7,621,956 | B2 | * | 11/2009 | Paul et al. | 623/17.15 |
| 7,828,847 | B2 | * | 11/2010 | Abdou | 623/17.13 |
| 2003/0040802 | A1 | * | 2/2003  | Errico et al. | 623/17.14 |
| 2004/0024460 | A1 | * | 2/2004  | Ferree | 623/17.12 |
| 2004/0138749 | A1 | * | 7/2004  | Zucherman et al. | 623/17.11 |
| 2004/0143332 | A1 | * | 7/2004  | Krueger et al. | 623/17.14 |
| 2004/0243240 | A1 | * | 12/2004 | Beaurain et al. | 623/17.14 |
| 2005/0033435 | A1 |   | 2/2005  | Belliard et al. |  |
| 2005/0043800 | A1 |   | 2/2005  | Paul et al. |  |
| 2005/0143820 | A1 | * | 6/2005  | Zucherman et al. | 623/17.11 |
| 2006/0041313 | A1 | * | 2/2006  | Allard et al. | 623/17.15 |
| 2006/0041314 | A1 | * | 2/2006  | Millard | 623/17.16 |
| 2006/0114646 | A1 |   | 6/2006  | Koibuchi et al. |  |

(Continued)

FOREIGN PATENT DOCUMENTS
WO   WO 2007/094923   8/2007

OTHER PUBLICATIONS
European Search Report for Application No. EP 09 16 4381; Place of Search München; Date of Completion of the Search, Oct. 14, 2009.

*Primary Examiner* — Kevin T Truong
*Assistant Examiner* — Zade Coley
(74) *Attorney, Agent, or Firm* — RatnerPrestia

(57) ABSTRACT

An intervertebral disk prosthesis system, which is used for forming an artificial intervertebral disk and comprises a first and a second prosthesis component wherein each of the two prosthesis components comprises a first and a second vertebral body contacting element for placement on neighboring vertebral bodies bounding an intervertebral disk space of a spinal column and a joint element that is mounted between and is moveable relative to at least one of the first and second vertebral body contacting elements, attains a substantially natural range of motion independent of the positioning of the two prosthesis components relative to each other and to the neighboring vertebral bodies. Each prosthesis component has a ball joint formed between the first and second vertebral body contacting elements.

77 Claims, 12 Drawing Sheets

U.S. PATENT DOCUMENTS

| | | |
|---|---|---|
| 2006/0229725 A1* | 10/2006 | Lechmann et al. ........ 623/17.11 |
| 2006/0235526 A1* | 10/2006 | Lemaire .................... 623/17.14 |
| 2006/0259147 A1* | 11/2006 | Krishna et al. ............. 623/17.15 |
| 2006/0265071 A1 | 11/2006 | Richelsoph |
| 2007/0083267 A1* | 4/2007 | Miz et al. ................... 623/17.13 |
| 2007/0118223 A1* | 5/2007 | Allard et al. ............... 623/17.13 |
| 2007/0191958 A1* | 8/2007 | Abdou ....................... 623/17.16 |
| 2007/0213821 A1 | 9/2007 | Kwak et al. |
| 2007/0233255 A1 | 10/2007 | Song et al. |
| 2008/0133013 A1* | 6/2008 | Duggal et al. ............. 623/17.16 |
| 2008/0215155 A1* | 9/2008 | de Villiers et al. ......... 623/17.16 |
| 2008/0221691 A1* | 9/2008 | Chaput et al. ............. 623/17.16 |
| 2009/0005874 A1* | 1/2009 | Fleischmann et al. ..... 623/17.16 |
| 2009/0076616 A1* | 3/2009 | Duggal et al. ............. 623/17.16 |

* cited by examiner

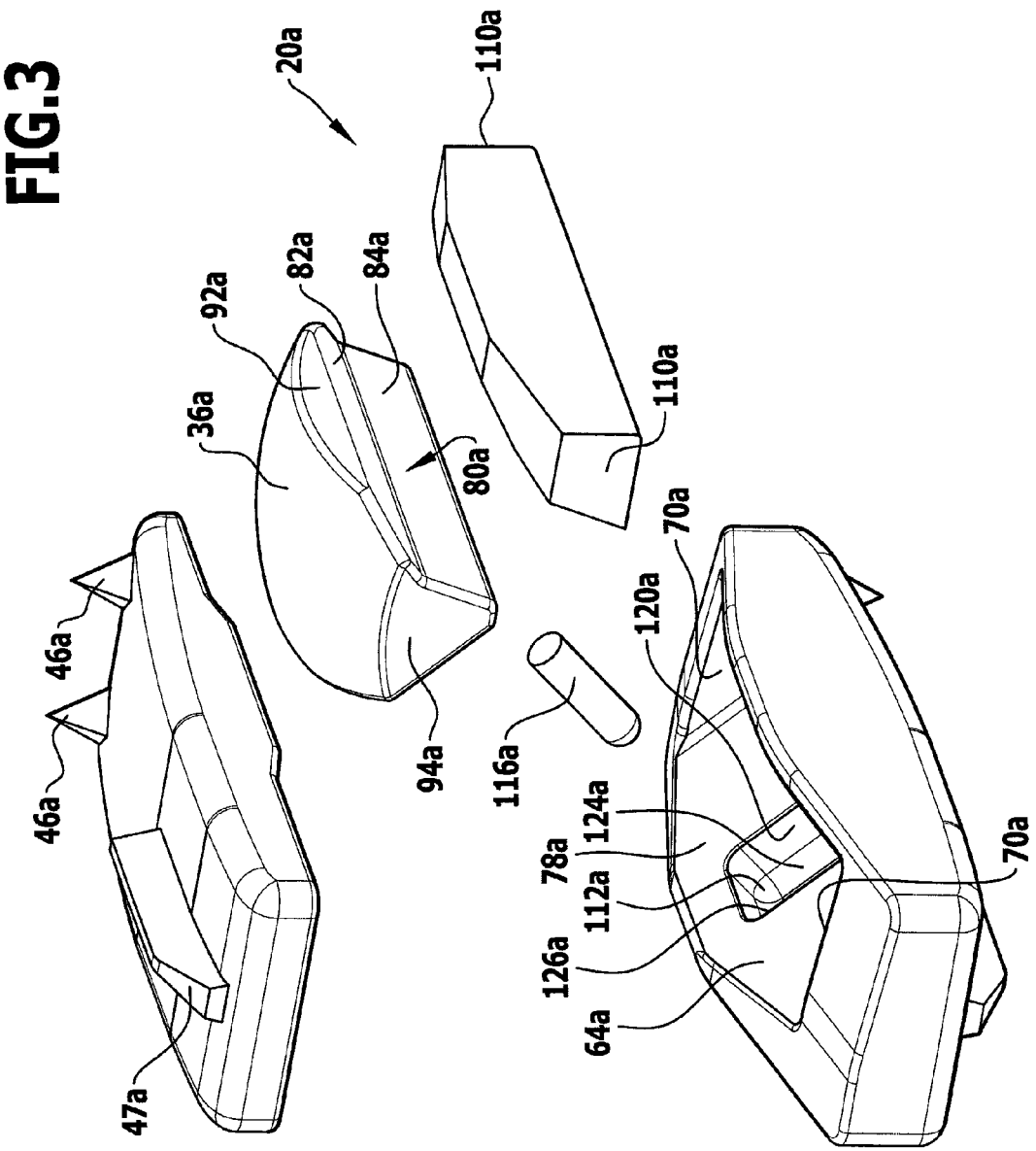

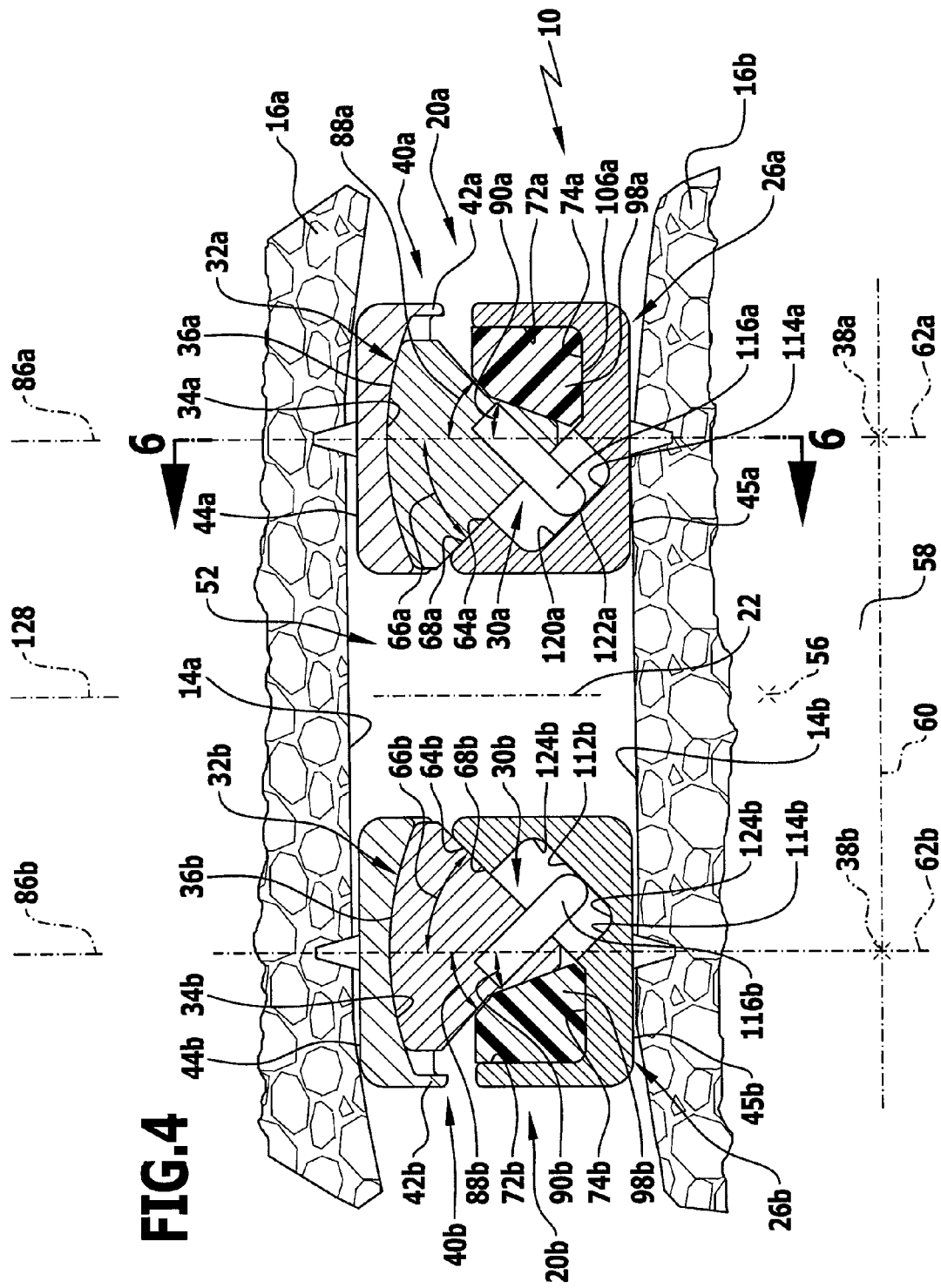

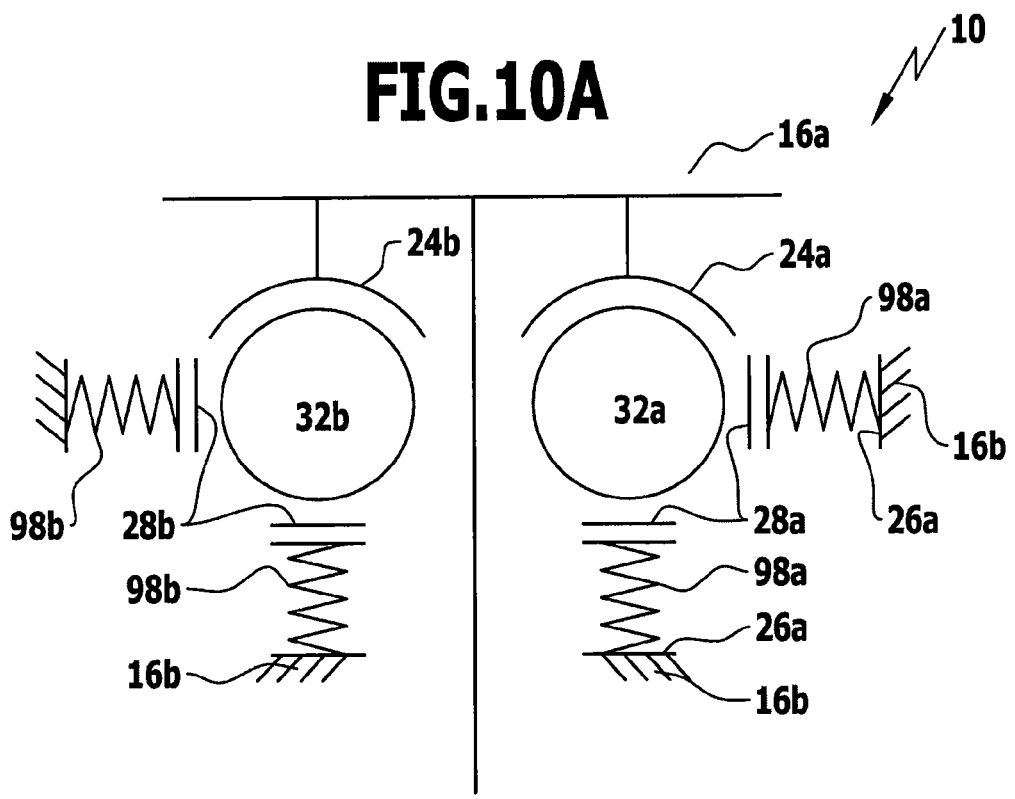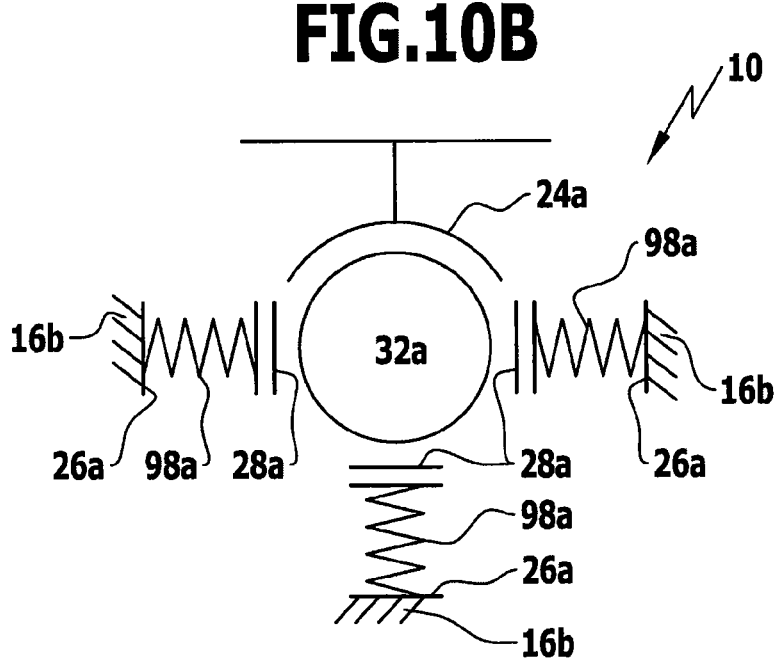

INTERVERTEBRAL DISK PROSTHESIS SYSTEM

CROSS-REFERENCE TO RELATED APPLICATION

This application claims priority under 35 U.S.C. §119 to German Patent Application No. 10 2008 032 691.7 filed Jul. 3, 2008, the contents of which is incorporated herein by reference in its entirety and for all purposes.

FIELD OF THE INVENTION

The present invention relates to an intervertebral disk prosthesis system for forming an artificial intervertebral disk generally, and more specifically to an intervertebral disk prosthesis system for forming an artificial intervertebral disk comprising a first prosthesis component and a second prosthesis component which is independent of the first prosthesis component, wherein each of the two prosthesis components comprises a first and a second vertebral body contacting element for placement on neighboring vertebral bodies which bound an intervertebral disk space in a spinal column and a joint element that is mounted in moveable manner relative to at least one of the first and second vertebral body contacting elements.

BACKGROUND OF THE INVENTION

An intervertebral disk prosthesis system as described in the outset is known from US 2007/0191958 A1 for example. The advantage of intervertebral disk prosthesis systems of this type is that they can be implanted into a patient's body via a posterior point of entry. In contrast to intervertebral disk prostheses comprising just a single prosthesis component which, in accord with current standard practice, are implanted via an anterior point of entry, large vessels do not need to be mobilized in order to reach the intervertebral disk space in the case of a posterior point of entry. In consequence, damage to the vessels can be prevented and any subsequently necessary revision of the intervertebral disk prosthesis system is thereby simplified. Furthermore, the use of a posterior point of entry has the advantage that the decompression of the spinal cord or the nerve roots that is frequently required can be effected simultaneously in the course of the surgical treatment. Moreover, any existing facet arthrosis can also be treated dorsally at the same time.

One problem encountered when implanting intervertebral disk prosthesis systems of the type described hereinabove via a posterior point of entry is the correct placement of the prosthesis components. A further challenge is presented by the distraction of the intervertebral disk compartment that is necessary during this, this also being referred to as the intervertebral disk space. Access thereto is only possible by retraction of the dura mater or the nerve root. A direct view into the intervertebral disk space is not possible so that resection of the intervertebral disk and placement of the prosthesis components must be effected along curved paths and this has to be done quasi "blindly" by the operating surgeon. Should two prosthesis components be inserted independently of one another into the intervertebral disk space, these then not being connected directly to one another but only being connected indirectly via the vertebral bodies that border onto the intervertebral disk space, then it is important that the prosthesis components be positioned relative to each other in a precise pre-defined manner. This is especially necessary in order to achieve as large a physiological degree of movement as possible, the so-called "Range of Motion" (ROM), for the intervertebral disk prosthesis system as well.

It is therefore desirable to provide an intervertebral disk prosthesis system that a substantially natural range of motion of the intervertebral disk prosthesis system is attainable as independently as possible of the positioning of the two prosthesis components relative to each other and to the neighboring vertebral bodies.

SUMMARY OF THE INVENTION

In a first aspect of the invention, an intervertebral disk prosthesis system for forming an artificial intervertebral disk comprises a first prosthesis component and a second prosthesis component which is independent of the first prosthesis component. Each of the two prosthesis components comprises a first and a second vertebral body contacting element for placement on neighboring vertebral bodies which bound an intervertebral disk space of a spinal column and a joint element that is mounted between and is moveable relative to at least one of the first and second vertebral body contacting elements. Each prosthesis component comprises a ball joint that is mounted in moveable manner between the first and second vertebral body contacting elements.

BRIEF DESCRIPTION OF THE DRAWINGS

The foregoing summary and the following description may be better understood in conjunction with the drawing figures, of which:

FIG. 3: a further perspective exploded illustration of the prosthesis component of the intervertebral disk prosthesis system depicted in FIG. 2;

FIG. 4: a cross sectional view through the intervertebral disk prosthesis system in the basic position in the anterior direction;

FIG. 10A: a schematic sketch analogous to FIG. 9A depicting the principle of a further variant of an intervertebral disk prosthesis system;

FIG. 10B: a sketch analogous to FIG. 9B depicting the principle of the intervertebral disk prosthesis system shown in FIG. 10A;

DETAILED DESCRIPTION OF PREFERRED EMBODIMENTS OF THE INVENTION

Figure 1:
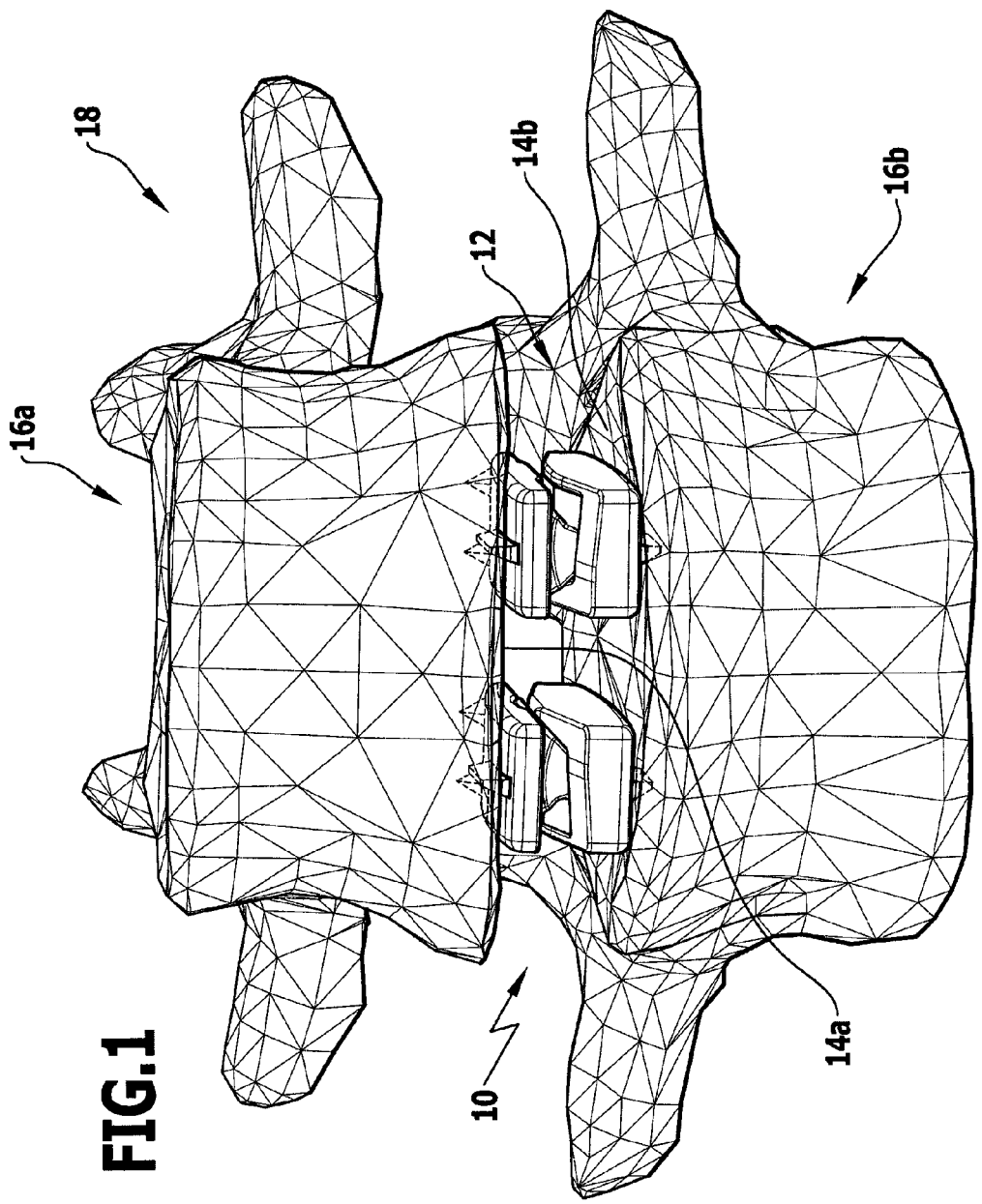
FIG. 1: shows a perspective overall view of a segment of a spinal column incorporating an intervertebral disk prosthesis system comprising two prosthesis components.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an intervertebral disk prosthesis system for forming an artificial intervertebral disk comprising a first prosthesis component and a second prosthesis component which is independent of the first prosthesis component, wherein each of the two prosthesis components comprises a first and a second vertebral body contacting element for placement on neighboring vertebral bodies which bound an intervertebral disk space of a spinal column and a joint element that is mounted between and is moveable relative to at least one of the first and second vertebral body contacting elements, wherein each prosthesis component comprises a ball joint that is mounted in moveable manner between the first and second vertebral body contacting elements.

An intervertebral disk prosthesis system of this type enables one to define an unambiguous rotational axis for a flexion or extension of the intervertebral disk that is being treated, independently of any precise positioning or orientation of the prosthesis components. Furthermore, prosthesis components of this type can also be formed in a simple manner in such a way that a common central point of rotation or articulation is independent of the actual positioning of the two prosthesis components. This is just not achieved, especially in the case of the intervertebral disk prosthesis system known from US 2007/0191958 A1, since ball joints in the form of sliding pairings were not provided therein and the radii of the joint surfaces resting upon one another were not even formed in a corresponding manner so that not only were rotational movements between the mutually contacting parts of the prosthesis component possible—but so too were translatory movements over corresponding bearings, this leading after extended usage of the intervertebral disk prosthesis system to increased wear and thus a shorter service life. Moreover, the proposed further development has the advantage that there is a larger area of contact between the mutually contacting parts whence lower surface pressures are attainable, this thereby helping to extend the life span of the intervertebral disk prosthesis system. In addition thereto, the production of a ball joint is simple.

Expediently, the first vertebral body contacting element and the associated joint element define the respective ball joint. This arrangement makes it possible to have a particularly compact structure for the two prosthesis components, and in particular, for the overall height thereof to be particularly small.

Furthermore, in accordance with a preferred embodiment of the invention, provision may be made for a guidance device for defining a superior swivel joint that is defined by both prosthesis components together for simultaneously rotating the two first vertebral body contacting elements relative to the two second vertebral body contacting elements about a common center of rotation which is located in a spatial region between the central points of the two ball joints. Independently of the orientation or positioning of the prosthesis components relative to each other and relative to the vertebral bodies defining the intervertebral disk space, the guidance device makes it possible to form a swivel joint which advantageously forms a joint having not just one degree of freedom of rotation, but expediently one which enables rotation of the first vertebral body contacting elements that are fixed relative to each other by the vertebral bodies about an arbitrary number of axes relative to the second vertebral body contacting elements. In particular, the guidance device can be formed in such a manner that the position of the common center of rotation is static or is variable in dependence on the deflection of the intervertebral disk prosthesis system from a basic position. In particular, the guidance device can predetermine a defined path for the center of rotation in the spatial region, for example, along a pre-defined spatial curve which can be two or three-dimensional. In particular, the center of rotation can define rotations about axes which deviate from an interconnecting straight line that connects the center points of the two ball joints to one another.

Expediently, the spatial region is bounded by two planes extending perpendicularly relative to a connecting line between the two center points of the two ball joints. A prerequisite of this type for the spatial region enables the intervertebral disk prosthesis system to be of particularly compact construction.

Advantageously, the intervertebral disk prosthesis system is formed in such a manner that the position of the center of rotation in the spatial region is changeable in a defined way in dependence on a deflection of the intervertebral disk prosthesis system from the basic position in which it is symmetrically configured. The functioning of this arrangement of the intervertebral disk prosthesis system approximates very closely to that of a natural intervertebral disk in which a center point of the joint can migrate relative to its position in the basic position in dependence on the relative movements of the neighboring vertebral bodies with respect to one another, for example, in the event of a flexion, an extension, lateral bending as well as rotation about a longitudinal axis of the spinal column or superimposed movements of the kind described. In summary then, it is thereby possible in a simple manner to form a swivel joint with movement-dependent translatory components of the position of the center point of the joint.

A particularly simple construction for the intervertebral disk prosthesis system can be achieved in that provision is made for a basic-position central plane to be located between the central points, said plane being oriented perpendicularly relative to the connecting line and the center of rotation being located thereupon at least in the basic position.

It is advantageous if the intervertebral disk prosthesis system is formed in such a manner that the spacing of the center of rotation from the basic position central plane increases with increasing deflection of the intervertebral disk prosthesis system from the basic position. Such an arrangement makes it possible to form an artificial intervertebral disk the manner of functioning of which is very close to that of a natural intervertebral disk.

The construction of the intervertebral disk prosthesis system is particularly simple and the production thereof is likewise simple, if it is formed in such a manner that the center of rotation is located on the basic position central plane independently of any deflection of the intervertebral disk prosthesis system from the basic position.

Expediently, a connecting line between the central points of the two ball joints defines a flexion/extension axis of the intervertebral disk prosthesis system. In particular, this connecting line is independent of the positioning of the prosthesis components relative to each other.

In order to ensure that the respective surface areas of the joint rest optimally upon one another, it is advantageous for the radius of the ball joints to be greater than the spacing of the two central points of the ball joints from each other.

The structure of the intervertebral disk prosthesis system is particularly simple, if the first and the second prosthesis components are formed such as to be mutually mirror-symmetrical in the basic position taken with respect to a symmetry running therebetween. This mirror-symmetrical formation does not mean that the prosthesis components have to be implanted mirror-symmetrically. Due to the mirror-symmetrical arrangement in particular, the effect can also be achieved that lateral tilting of the neighboring vertebral bodies relative to one another, thus for example, rotations about an axis of rotation running in the anterior-posterior direction, is carried out symmetrically.

Expediently, the connecting line in the basic position defines a common rotational axis of the intervertebral disk prosthesis system which runs in the lateral direction transverse to the symmetry axis. In particular, the common rotational axis enables a flexion/extension of that segment of the spinal column which is defined by the neighboring vertebrae in connection with the intervertebral disk prosthesis system.

It is expedient, if the plane of symmetry runs in the anterior-posterior direction of the intervertebral disk prosthesis system. When the intervertebral disk prosthesis system is implanted, the plane of symmetry may, in particular, be the median plane i.e. a sagittal plane passing through the center of the body.

In order to achieve particularly good support for the neighboring vertebral bodies, it is expedient if the longitudinal axes of the two prosthesis components are inclined with respect to the plane of symmetry or run parallel thereto. In dependence in particular on a state of the neighboring vertebral bodies, the two prosthesis components can then be implanted such that they are optimally placed.

In accordance with a further preferred embodiment of the invention, provision may be made for an axial rotational axis which includes the center of rotation and which, at least in a non-deflected basic position, runs in the plane of symmetry or parallel thereto and is perpendicular or substantially perpendicular to contact surfaces defined by the first and second vertebral body contacting elements. In particular, the expression an axial rotational axis is to be understood as being a rotational axis which defines a rotation about a longitudinal axis of the spinal column segment of the spinal column in the region of the neighboring vertebral bodies defined in connection with the intervertebral disk prosthesis system.

A ball joint can be formed between the first vertebral body contacting element and the joint element in a particularly simple manner if the first vertebral body contacting element defines a first joint surface, if the joint element defines a second joint surface which is formed in correspondence with the first joint surface, if the second joint surface forms a part of a spherical surface and if the first joint surface forms a part of a hollow ball.

A particularly simple structure for the guidance device of the intervertebral disk prosthesis system can be achieved, in particular, in that the guidance device on each prosthesis component comprises a guidance surface for guiding a movement of the two ball joints relative to the second vertebral body contacting element. In other words, this means that the two ball joints, which can be defined in particular by the first vertebral body contacting elements and the joint elements, are movable relative to the second vertebral body contacting elements in a defined manner in order to define the common center of rotation in this way. Hereby, it is particularly expedient if the guidance device ensures that the first and second surfaces of the joint fit flatly together independently of any relative orientation of the vertebral bodies bounding the intervertebral disk space.

The intervertebral disk prosthesis system can be formed with a particularly small number of parts if the guidance surface is formed such as to guide a movement of the respective joint element relative to the second vertebral body contacting element. In principle, this enables the two prosthesis components to be formed in each case from only three parts namely, the two vertebral body contacting elements and also a joint element that is mounted therebetween and is moveable relative to both vertebral body contacting elements.

Preferably, the guidance surface is formed on the joint element and/or on the second vertebral body contacting element. It is preferably formed in such a way that the joint element and the second vertebral body contacting element fit flatly together independently of any relative positioning of the two neighboring vertebral bodies.

It is advantageous if the second vertebral body contacting element defines a third joint surface and if the joint element defines a fourth joint surface which is formed in correspondence with the third joint surface and if the third and/or the fourth joint surface forms the guidance surface. This arrangement enables the intervertebral disk prosthesis system to have a particularly compact structure. In addition, particularly good guidance of the movement of the second vertebral body contacting element and the joint element relative to each other is attainable in this way.

Expediently, the guidance surface defines a joint plane. In particular, the joint plane can predefine the relative motion of the joint element and the second vertebral body element, in particular, by restricting the number of degrees of freedom of movement from the joint plane or transversely thereto.

In order to ensure that the first and second joint surfaces of the ball joints fit flatly together independently of the position of the center of rotation, it is expedient if the joint element is displaceable relative to the second vertebral body contacting element in parallel with the joint plane and/or is adapted to twist about an axis of rotation running perpendicularly relative to the joint plane. This arrangement makes it possible for the central points of the ball joints to be moved relative to each other in the requisite manner in order to maintain the long-term functionality of the intervertebral disk prosthesis system.

It is expedient if the joint plane is inclined at an angle of inclination relative to a longitudinal axis which extends in the direction of the first vertebral body contacting element in the basic position and is defined by the second vertebral body contacting element. Due to the inclination of the joint plane, the effect can be achieved that the central point of the ball joint can be moved relative to the second vertebral body contacting element in a desired or necessary manner in order to ensure that the overall positioning of the two ball joints on the two prosthesis components will be such that it is possible for the first and second joint surfaces to fit flatly together even when there is a change in the position of the center of rotation. Due to the inclined joint plane, the necessary degrees of freedom for matching the two prosthesis components are made available in a simple manner independently of the positioning of these components between the neighboring vertebral bodies.

Matching of the two prosthesis components relative to each other can be achieved expediently if the angle of inclination has a value within a range of 10° to 80°.

Preferably, the angle of inclination has a value in a range of 30° to 60°.

It is particularly advantageous, if the angle of inclination amounts to 45°. In particular, a symmetrical movement of the joint element relative to the second vertebral body contacting element can be predetermined in this way.

It is advantageous, if the third joint surface extends in the lateral direction and in the direction of the first vertebral body contacting element. Such a joint surface enables the joint element to, as it were, slide on the second vertebral body contacting element in the event of lateral bending of the two vertebral bodies relative to each other. In this way in particular, the spacing between the two vertebral body contacting elements can be altered in a defined manner in the event of a simultaneous, i.e. dependent transverse movement. Due to the specific inclination, the joint element can be moved in the direction of the second vertebral body contacting element, namely, in the case of the prosthesis component, the vertebral bodies can be moved towards one another on their side. In the case of the other prosthesis component, sliding of the joint element on the second vertebral body contacting element can then be effected in the sense that the spacing between the two vertebral body contacting elements is increased and, due to the dependent transverse movement, the joint element is shifted somewhat in the direction of the other prosthesis component.

Furthermore, in accordance with a further preferred embodiment of the invention, provision may be made for a movement limiting device for the purposes of limiting any relative movement of the joint element and the second vertebral body contacting element of the respective prosthesis component relative to each other. In this way, a deflection and, for example, a maximum angle of inclination of the two vertebral bodies relative to each other can be limited by the intervertebral disk prosthesis system. In particular, the range of motion of the common center of rotation of the intervertebral disk prosthesis system can be defined and also limited in this way.

The movement limiting device can be formed in a particularly simple manner if it comprises a first and a second stop member, if the joint element comprises the one of the stop members and if the second vertebral body contacting element comprises the other one of the two stop members, if the first stop member defines a surface region of the joint plane and, if the second stop member is freely moveable within the surface region. Due to the specific arrangement of the two stop members which thus co-operate for the purposes of limiting the movement of the joint element and the second vertebral body contacting element, the surface region within which the joint element and the second vertebral body contacting element are freely moveable relative to each other can be defined by the shaping of the first stop member and that of the second stop member.

The intervertebral disk prosthesis system is particularly simple in structure and the production process is particularly simple too, if the surface region is rectangular or substantially rectangular. Self-evidently, it would also be conceivable for any other shape to be selected, such as having a circular or oval cross section for example. A uni-dimensional configuration is also conceivable, be this along a straight-line or a curved or multiply-curved guide path.

In order to permit relative movement of the joint element and the appertaining second vertebral body contacting element in a simple manner, it is advantageous if a cross section of the first stop member parallel to the joint plane is greater than the cross section of the second stop member parallel to the joint plane. The second stop member can then be introduced into the first stop member, but nevertheless, it has adequate freedom of movement in at least one spatial direction, although preferably in two, in order to permit the desired relative movement between the joint element and the second vertebral body contacting element. In particular thereby, such movement may be translatory and rotary and it could also be superimposed translatory and rotary movements of the joint element and the second vertebral body contacting element relative to each other.

Expediently, the second stop element is oriented perpendicularly or substantially perpendicularly relative to the joint plane. This arrangement permits of a particularly compact structure for the prosthesis components. Furthermore, it is thereby ensured that a limiting force that is effective due to the mutual striking of the stop members is directed parallel to the joint plane and thus perpendicularly to a direction prescribed by the second stop member.

Preferably, the first stop member is in the form of a recess and the second stop member is in the form of a projection which protrudes into the recess. A movement of the components of the intervertebral disk prosthesis system bearing the stop members is then possible to the extent defined by the stop members by virtue of their shape.

The production of the intervertebral disk prosthesis system is simplified still further if the projection is in the form of a stop pin.

In principle, it would be conceivable for the cross section of the projection to have any arbitrary shape. Preferably however, the projection has a circular cross section. The projection can then, in particular, be in the form of a cylindrical pin and be arranged or formed on the joint element or on the second vertebral body contacting element.

Preferably, a free end of the projection is in the form of a hemisphere. In this way in particular, the projection can be formed such as to be edge-free and, in a manner corresponding to that of a first stop member, it can have correspondingly rounded inner edges in order to prevent insofar as possible the stop members from resting on one another along a line which could lead to tilting of the prosthesis parts.

For the purposes of preventing the stop members from tilting together in extreme positions, it is expedient if the inner edges of the recess are rounded in correspondence with the cross section and/or the shape of the free end of the projection. Furthermore, this has the advantage that the production of the recess is simplified since it can be produced with the aid of a ball-type milling tool for example.

The stability of the intervertebral disk prosthesis system can be increased in a simple manner in that the joint element comprises the second stop member. In particular when the joint element is made smaller than the second vertebral body contacting elements, the first stop member that is in the form of a recess for example can ideally be formed on the second vertebral body contacting element since there is frequently more space available there.

For the purposes of simplifying the production process, it is expedient if the joint element and the second stop member are in two-piece form and if they are inseparably connected to one another. For example, they can be stuck together, or bolted or welded to one another.

Advantageously, the joint element defines a fifth joint surface which rests directly or indirectly against the second vertebral body contacting element. In particular, the joint element can be formed such as to be substantially wedge-shaped in cross section so that the side faces of the fourth and fifth joint surfaces define a wedge which has a further exterior surface in the form of the second spherical joint surface for the purposes of forming the ball joint.

Sliding contact movements in different directions can be realized in a simple manner, if the fifth joint surface is inclined relative to the fourth joint surface. The angle of inclination between the joint surfaces can lie in a range of 45° to 135° for example.

A particularly stable configuration of the intervertebral disk prosthesis system can be achieved if a line of intersection of the planes defined by the fourth and fifth joint surfaces runs in the anterior-posterior direction. This applies particularly in regard to the basic position of the intervertebral disk prosthesis system in which it is not deflected. Preferably the line of intersection runs perpendicularly or substantially perpendicularly relative to the connecting straight lines or connecting line interconnecting the central points of the ball joints.

In order to achieve optimal support for the joint elements on the second vertebral body contacting element, it is expedient if the fourth joint surface is inclined in the medial direction and if the fifth joint surface is inclined in the lateral direction. In this way, it can be ensured that, in dependence on a movement of the neighboring vertebral bodies relative to each other, the joint element will always rest against the fourth joint surface independently of the angle of inclination of the vertebral bodies relative to each other. Stable support of and optimal guidance for the mutually-contacting and guided parts of the prosthesis components can thus be achieved at the same time.

Expediently, the fifth joint surface has two joint surface regions which are inclined relative to each other, said joint surface regions defining joint surface region planes that are inclined relative to each other. Such an arrangement is advantageous, in particular, when the fifth joint surface cooperates with a damping or resetting member in order to damp a movement of the joint element in the direction of the second vertebral body contacting element. Due to the two inclined joint surface regions, optionally different spring rates of a damping element can be activated in dependence on the direction of the force introduced by the joint element.

In order to obtain additional positive guidance, it is expedient if the one of the joint surface regions is inclined relative to a longitudinal axis defined by the second vertebral body contacting element to a greater extent than the joint plane and if the other one of the joint surface regions is inclined relative to the longitudinal axis to a lesser extent than the joint plane. In this way, the two joint surface regions define the side faces of a wedge-shaped recess which can provide good guidance for a relative movement in the anterior-posterior direction in particular.

It is expedient, if an angle of inclination of the one joint surface region relative to the longitudinal axis lies within a range of 40° to 60° and if an angle of inclination of the other joint surface region relative to the longitudinal axis lies in a range of 10° to 30°. In particular here, a longitudinal axis is to be understood as being the longitudinal axis that extends in the direction of the first vertebral body contacting element and is defined by the second vertebral body contacting element. The indicated ranges for the angle of inclination enable the joint element to be produced in a simple manner and, in addition, help to prevent tilting thereof with respect to the second vertebral body contacting element.

The structure of the second joint element is particularly simple, if the line of intersection of the joint surface region planes runs in the anterior-posterior direction. In particular, this enables optimal guidance to be provided in the event of flexion or extension of the spinal column.

Furthermore, in accordance with a preferred embodiment of the invention, provision may be made for a re-setting device for returning the two ball joints of the prosthesis components back into the basic position from a position in which the joint is deflected from the basic position. The re-setting device can also serve, in particular, as a damping device in order to counteract the compressive force that is introduced by the two adjacent vertebral bodies and is effective on the intervertebral disk space, and it can also serve to prevent the parts of the prosthesis components from striking against each other.

Expediently, the re-setting device is formed in such a manner that, in the basic position of the intervertebral disk prosthesis system, the second stop member is spaced from the lateral boundary surfaces of the first stop element which defines the surface region. This arrangement makes it possible for the joint element to move relative to the second vertebral body contacting element freely in all of the directions that are permitted by the surface region. In particular, starting from the basic position, it is then possible to move the joint element relative to the second vertebral body element directly against the effect of the re-setting device, for example, as a result of the introduction of a force via the first vertebral body contacting element into the joint element.

It is advantageous if the re-setting device is formed in such a manner that, in the basic position of the intervertebral disk prosthesis system, the joint element is in contact therewith out having to bias the re-setting device. The basic position can, in particular, be a not yet implanted position of the parts of the intervertebral disk prosthesis system relative to one another or it could also be an implanted position.

A particularly simple structure for the intervertebral disk prosthesis system can be obtained in the event that the re-setting device engages with the fifth joint surface. In particular, the re-setting device can be formed in such a manner that it engages exclusively with the fifth joint surface of the joint element and otherwise is supported on the second vertebral body contacting element.

Preferably, the re-setting device is formed in such a manner that, in the basic position of the intervertebral disk prosthesis system, the second vertebral body contacting element is in contact therewith out having to bias the re-setting device. In particular, it is possible in this way to form a prosthesis component wherein the joint element is supported directly on the second vertebral body element on the one hand, and is supported indirectly through the intermediary of the re-setting device inserted therebetween on the other so that a movement parallel to the joint surface can be damped by appropriately effective forces.

Optionally, it is expedient if the re-setting device is spring biased into the basic position. Again thereby, the basic position can determine an implanted or a non-implanted position of the intervertebral disk prosthesis system. The spring bias has the advantage that even when there is a movement of the joint element in a direction away from the second vertebral body contacting element, further contact between the re-setting device and the joint element is still initially maintained, i.e. there will be no immediate separation of the parts from one another.

Advantageously, the joint element is movable from the basic position in the lateral direction against the effect of the re-setting device. This arrangement permits deviations from a parallel alignment of the prosthesis components in the anterior-posterior direction to be compensated. In this way in particular, the re-setting device can have an additional effect on the positioning of the center of rotation of the intervertebral disk prosthesis system and actively prevents lifting of the joint elements of the prosthesis components from the respective second vertebral bodies.

In particular, optimal damping of the intervertebral disk prosthesis system in the axial direction can be achieved if the joint element is movable from the basic position in the direction of the second vertebral body contacting element against the effect of the re-setting device. In particular thereby, a wedge-shaped arrangement of the second joint element can lead to a defined application of force and can prevent the prosthesis components, parts made of a metal for example, from striking against one another.

In particular for the purposes of stabilising the spinal column segment comprising the intervertebral disk prosthesis system, it is advantageous if the joint element is movable from the basic position in the anterior direction against the effect of the re-setting device. In this way in particular, a flexural movement of the spinal column can be selectively damped.

In an analogous manner, it is advantageous if the joint element is movable from the basic position in the posterior direction against the effect of the re-setting device. In this way, selective damping can be initiated and achieved in the event of an extension movement of the spinal column segment comprising the intervertebral disk prosthesis system.

It is advantageous, if the re-setting device comprises at least one resetting member which engages with the joint element on the one hand and with the second vertebral body contacting element on the other. In particular, the at least one resetting member can be arranged in such a manner that a movement of a guided joint element resting against the second vertebral body contacting element away from the first vertebral body contacting element in the direction of the second vertebral body contacting element is damped. In this way moreover, the re-setting device can be constructed in a particularly simple manner.

In particular in the case of a joint surface that is inclined with respect to a plane of symmetry of the intervertebral disk prosthesis system, it is advantageous if the re-setting device comprises two resetting members which define directions of force that are linearly mutually independent. In other words, this means that the two directions of force can each be broken down into two components of which only one extends in the same direction or in mutually opposed directions. In particular, linearly independent is to be understood in the mathematical sense.

The structure of the re-setting device is particularly simple, if it comprises just a single resetting member.

The intervertebral disk prosthesis system can be formed in a particularly stable manner if the at least one resetting member has a joint element contact surface which rests against the fifth joint surface in the basic position. In this way, the joint element can be supported in the first place on the fourth joint surface of the second vertebral body contacting element and secondly on the at least one resetting member, namely, in the basic position as well as in a position in which the resetting member is compressed against the effect of a force introduced by the joint element.

Advantageously, the joint element contact surface comprises two joint element contact surface sections which define joint element contact surface planes that are inclined relative to each other. In particular, this has the advantage that when the joint element has correspondingly inclined joint surface region planes, these rest flatly against the joint element contact surface sections and so minimum surface pressures can be achieved.

In particular, it is advantageous if the joint element contact surface planes extend parallel to the joint surface region planes. In this way, the joint element can rest flatly on the resetting member in a simple manner.

Preferably, the joint element contact surface planes coincide with the joint surface region planes in the basic position. In other words, this means that the fifth joint surface can rest flatly or substantially flatly on the at least one resetting member in the basic position.

It is expedient for the joint element to be made of polyetheretherketone (PEEK), cobalt chrome, implant steel, titanium, ceramic, polyethylene (PE), silicone, hydrogel, polytetrafluorethylene (PTFE) or polyethylene terephthalate (PET). In particular, the resilient forms of the aforesaid materials are of outstanding interest for the purposes of additionally associating damping properties with the joint element. In this way for example, the joint element itself can also form a part of the re-setting device, for example, a part of the resetting member itself.

Advantageously, the first and/or the second vertebral body contacting element are made of polyetheretherketone (PEEK), cobalt chrome, implant steel, titanium and/or a ceramic. The choice of the aforesaid materials makes it possible to form sliding pairs with the joint element consisting of the same materials.

Preferably, the first and/or the second and/or the third and/or the fourth and/or the fifth joint surface are provided with a ceramic coating. Such a coating, which exhibits friction-reducing properties, is preferably applied to the joint elements and/or to the first and/or the second vertebral body contacting elements when they themselves are not made of a ceramic material in order to form defined ceramic sliding pairs of high abrasion resistance.

The structure of the re-setting device is particularly simple if the resetting member is formed from at least one resilient, spring-like spring element. In particular, provision may be made for a plurality of spring elements which are effective in different spatial directions that may also, in particular, define linearly independent directions.

Furthermore, it can also be advantageous for the at least one resilient spring element to be formed from an elastomer or to be in the form of a coil spring, a hydrogel element or a hydraulic cylinder. In dependence on the desired shape of the resetting member or else of the joint element and the second vertebral body contacting element, the previously mentioned variants of the resetting member are particularly well suited for forming a compact intervertebral disk prosthesis system.

A particularly compact arrangement of the intervertebral disk prosthesis system can be achieved in particular if the joint element forms or comprises the resetting member. In particular, the joint element can be formed in one-piece manner or be in two-piece form whereby the one part of the joint element can define the second joint surface, whilst the other part of the joint element can define the resetting member.

It is expedient, if at least one of the vertebral body contacting elements comprises at least one anchoring element for anchoring the at least one vertebral body contacting element to a vertebral body. In this way, the prosthesis components can be prevented from being able to move relative to the vertebral bodies. A relative movement between the two vertebral bodies can thus be transferred in a defined manner from the first vertebral body contacting element to the joint element and from the latter to the second vertebral body contacting element or vice versa.

The intervertebral disk prosthesis system is of particularly simple construction if the at least one anchoring element is in the form of a projection.

Particularly secure anchoring of the vertebral body contacting elements to the vertebral bodies can be achieved in a simple manner when the projection is wedge shaped or if it is pointed. In particular, it could also be in the form of a cone or be pyramid-shaped.

The stability of the vertebral body contacting elements can be increased in a simple manner if the at least one anchoring element is formed in one-piece manner with the at least one vertebral body contacting element.

Furthermore, in particular for simplifying the process of implanting the intervertebral disk prosthesis system, it is conceivable for the at least one anchoring element to be in the form of a separate component which is connectable to the at least one vertebral body contacting element.

The vertebral body contacting elements can be anchored to the vertebral bodies in a particularly simple manner if the at least one anchoring element is in the form of a screw or a clamp. Preferably, appropriate recesses or seatings for the at least one anchoring element are provided in the vertebral body contacting elements.

Advantageously, the intervertebral disk prosthesis system comprises a ball joint stop device for limiting any relative movement of the joint elements and the associated first vertebral body contacting elements relative to each other.

The ball joint stop device can be formed in a particularly simple manner if it comprises a projection which is formed on the joint element and/or on the first vertebral body contacting element. In each case, the projection can form a stop member for the other part of the prosthesis component.

Especially for the purposes of limiting a lateral bending movement of the intervertebral disk prosthesis system in a defined manner, it is advantageous if the projection is in each case arranged laterally at the side of the respective prosthesis component. In particular, a range of motion of the intervertebral disk prosthesis system simulating a natural range of motion can be defined in this way.

Furthermore, in accordance with a further preferred embodiment of the invention, provision may be made for the ball joint stop device to be formed in one-piece manner with the respective joint elements and/or the respective first vertebral body contacting elements. This arrangement has a positive effect upon the stability of the components of the prosthesis components. Furthermore, a particularly compact design for the prosthesis components can also be achieved in this way.

An intervertebral disk prosthesis system bearing the general reference symbol 10 for insertion into an intervertebral disk space 12 after a resection or a partial resection of a natural intervertebral disk is illustrated in FIGS. 1 to 8. The intervertebral disk space 12 is bounded laterally by the joint surfaces 14a and 14b of neighboring vertebral bodies 16a and 16b of a spinal column 18.

The intervertebral disk prosthesis system 10 comprises two prosthesis components 20a and 20b which are formed mirror-symmetrically of a median plane 22. The prosthesis component 20a is preferably implanted in the right-hand half of the patient's body whilst the prosthesis component 20b is preferably implanted in the left-hand half of the patient's body.

Figure 2:
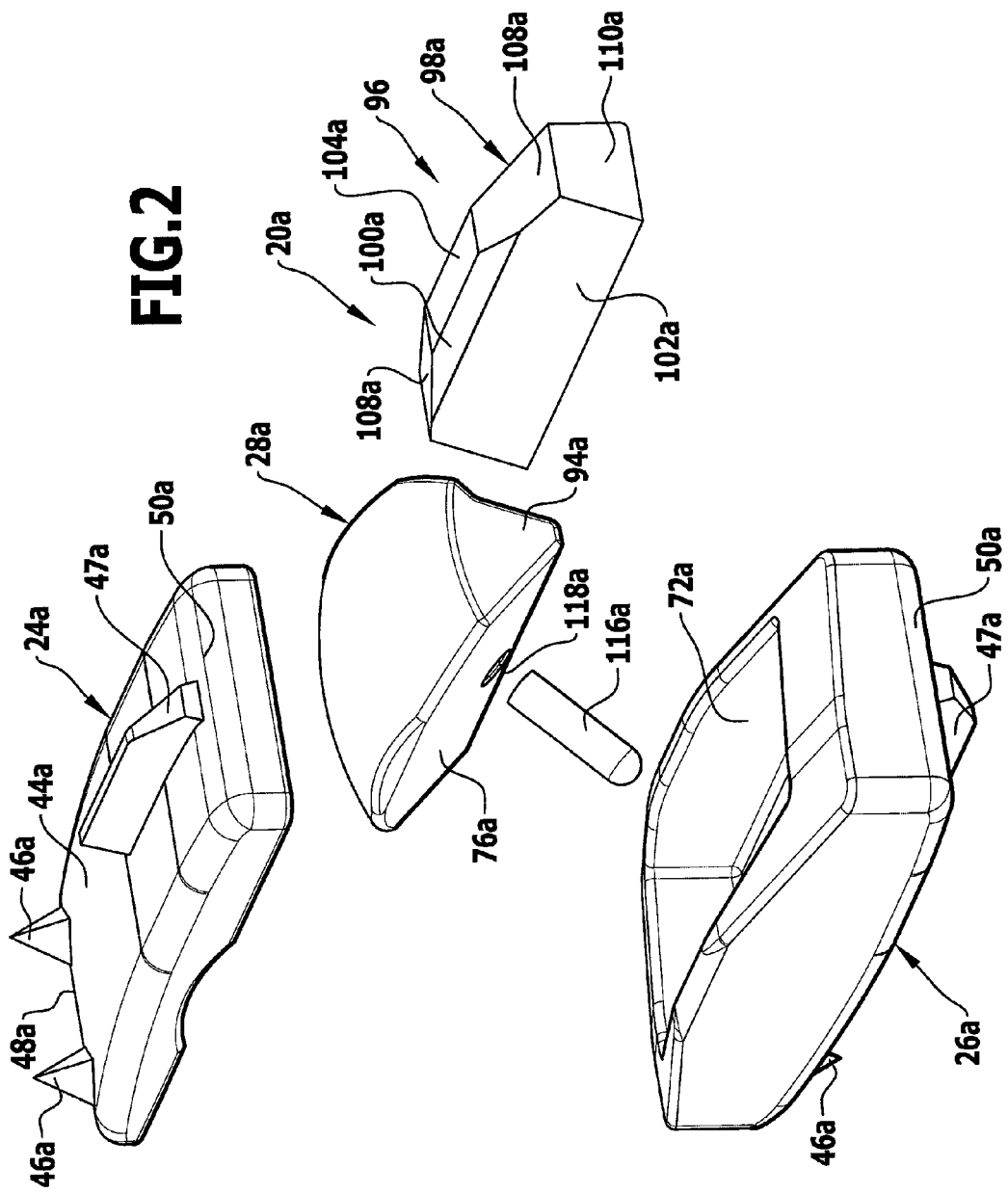
FIG. 2: a perspective exploded illustration of a right-hand side prosthesis component of the intervertebral disk prosthesis system.

The structure of the prosthesis components 20 and 22 is described in more detail hereinafter with respect to FIGS. 2 and 3 in particular. For reason of clarity, identical or mirror-symmetrical elements of the prosthesis components 20a and 20b are provided with the same reference symbols and differ only in regard to the final letters a and b. Due to the mirror-symmetrical construction of the prosthesis components 20a and 20b, the following detailed description is restricted to the arrangement of the right-hand side prosthesis component 20a.

The prosthesis component 20a comprises a first vertebral body contacting element 24a, a second vertebral body contacting element 26a and also a joint element 28a which is mounted in moveable manner on both vertebral body contacting elements 24a and 26a. Moreover, the prosthesis component 20a comprises a movement limiting device 30 for limiting relative movement between the joint element 28a and the second vertebral body contacting element 26a. Furthermore, the prosthesis component 20a comprises a ball joint 32a which is formed between the first and second vertebral body contacting elements 24a and 26a. The ball joint 32a is defined by the first vertebral body contacting element 24a and the associated joint element 28a. For the purposes of forming the ball joint 32a, the first vertebral body contacting element defines a first joint surface 34a and the joint element 28a defines a second joint surface 36a which is formed in a manner corresponding to that of the first joint surface 34a. The second joint surface 36a forms a part of a spherical surface and the first joint surface 34a forms a part of a hollow ball surface. The radii of the spherical surface and the hollow ball surface are identical and define a central point 38a of the ball joint 32a which lies substantially in the interior of the vertebral body 16b after an implantation process. The first joint surface 34a faces in the direction of the joint surface 14b, the second joint surface 36a in the direction of the joint surface 14a.

Moreover, the prosthesis component 20a is equipped with a ball joint stop device 40a for limiting a relative movement of the joint element 28a and the associated first vertebral body contacting element 24a relative to each other. The ball joint stop device 40a comprises a projection 42a which is formed laterally on the side of the first vertebral body contacting element 24a and it is substantially in the form of an edge or flange pointing in the direction of the second vertebral body contacting element 26a. The projection 42a limits the movement of the joint element 28a in the lateral direction or a movement of the first vertebral body contacting element 24a in the direction of the prosthesis component 20a. Optionally, the projection 42a could also be arranged on the first vertebral body contacting element at the medial side. Optionally, the ball joint stop device 40a could also comprise a not illustrated projection on the joint element 28a which co-operates with the first vertebral body contacting element 24a in a similar or analogous manner. It can be arranged on the joint element 28a at the lateral or medial side. Preferably, the projection 42a is formed in one-piece manner with the first vertebral body contacting element 24a as in the exemplary embodiment of the intervertebral disk prosthesis system 10 illustrated in the Figures.

Overall, the first vertebral body contacting element 24a is substantially plate-like and comprises a joint contact surface 44a which is slightly convex in the direction of the joint surface 14a and which is adapted to be placed thereon. In order to be able to ensure secure anchoring of the first vertebral body contacting element 24a to the vertebral body 16a, there are provided anchoring elements 46a and 47a which protrude substantially perpendicularly from the joint contact surface 44a in the direction of the joint surface 14a. Two mutually spaced pyramid-shaped anchoring elements 46a are arranged in the vicinity of a posterior rear edge 48a, the anchoring element 47a is in the form of an anchoring rib or a wedge-shaped projection which, commencing from an anterior front edge 50a, extends over approximately half the length of the first vertebral body contacting element 24a in the anterior-posterior direction. Overall, the anchoring element 47a is formed in the manner of a fin.

In an analogous manner, anchoring elements 46a and 47a are also formed on the second vertebral body contacting element 26a, namely, two anchoring elements 47a in the vicinity of a rear edge 48a of the flat, cuboidal second vertebral body contacting element 26a which are in the form of pyramid-shaped projections that protrude perpendicularly from a joint contact surface 45a. The joint contact surface 45a is curved slightly convexly in the direction of the vertebral body 16b in analogous manner to the joint contact surface 44a. Commencing from a front edge 50a of the second vertebral body contacting element 26a, a rib-like or fin-like projection, which forms the anchoring element 47a, extends on the joint contact surface 45a in the anterior-posterior direction over approximately half the extent of the second vertebral body contacting element 26a. Each of the anchoring elements 47a is slightly wedge-shaped and the cross section thereof tapers in a direction away from the respective vertebral body contacting element 24a or 26a. Optionally, provision could also be made for not illustrated anchoring elements in the form of separate components that are connectable to the vertebral body contacting elements 24a or 26a. Conceivable in particular, are screws or clips which can preferably be introduced or realised in correspondence with recesses or seatings in the vertebral body contacting elements 24a or 26a.

Figure 6:
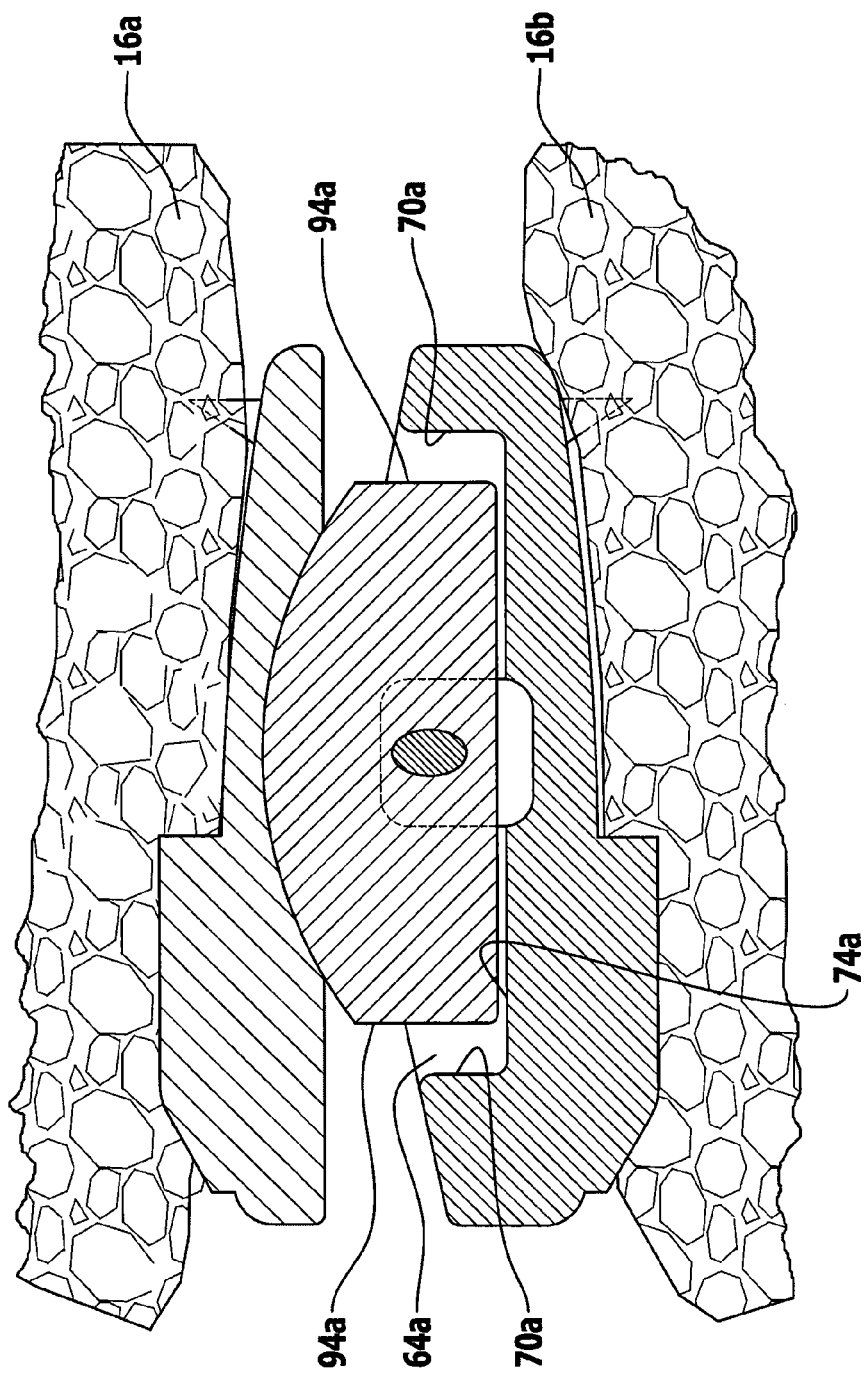
FIG. 6: a sectional view along the line 6-6 in FIG. 4.

Furthermore, the intervertebral disk prosthesis system 10 comprises a guidance device 52 for defining a higher-order swivel joint 54 that is defined by the prosthesis components 20a and 20b together for simultaneously twisting the two first vertebral body contacting elements 24a and 24b relative to the two second vertebral body contacting elements 26a and 26b about a common center of rotation 56. The center of rotation 56 lies in a spatial region 58 between the central points 38a and 38b of the ball joints 32a and 32b. As is illustrated in FIGS. 1, 4 and 6, the spatial region 58 is bounded at least in the basic position of the intervertebral disk prosthesis system 10 by two planes 62a and 62b which run perpendicularly relative to a connecting line 60 between the two central points of the two ball joints 32a and 32b.

The guidance device 52 comprises a respective guidance surface 64a and 64b on each prosthesis component 20a and 20b for guiding the movement of the two ball joints 32a and 32b relative to the respective second vertebral body contacting element 26a and 26b. The guidance surfaces 64a and 64b are formed for the purposes of guiding the movement of the respective joint elements 28a and 28b relative to the second vertebral body contacting element 26a and 26b. In the exemplary embodiment of the intervertebral disk prosthesis system 10 illustrated in the Figures, they are formed on the second vertebral body contacting element 26a or 26b, but they could also be formed however on the joint element 28a or 28b. The guidance surfaces 64a and 64b are inclined relative to the planes 62a and 62b at a respective angle of inclination 66a and 66b, namely, in each case, in the lateral direction and pointing towards the respective first vertebral body contacting element 24a and 24b. The angle of inclination 66a, 66b amounts to 45° in the intervertebral disk prosthesis system 10 illustrated in the Figures, but it could also lie in a range of 20° to 70°.

The guidance surface 64a, 64b forms a side boundary surface of a seating 68a in the second vertebral body contacting element 26a or 26b for the respective joint element 28a and 28b. The guidance surface 64a, 64b is bounded on the anterior side as well as on the posterior side by inner, mutually opposed end faces 70a, 70b which run substantially parallel to each other and perpendicular with respect to the planes 62a and 62b. A lateral inner side face 72a, 72b is oriented perpendicularly or substantially perpendicularly with respect to the end faces 70a, 72b and runs substantially parallel to or in parallel with the planes 62a and 62b. Furthermore, the seating 68a, 68b comprises a substantially elongated rectangular bottom surface 74a, 74b which has edges in common with the respective guidance surface 64a and 64b as well as with the end faces 70a and 70b and also the side faces 72a and 72b.

The joint element 28a defines a fourth plane joint surface 76a and the second vertebral body contacting element 26a defines a third joint surface 78a which forms the guidance surface 64a. The cross section of the joint element 28a is substantially wedge-shaped or prism-shaped, as illustrated in FIG. 4 for example. Two side faces of the joint element 28a are formed by the previously described second joint surface 36a and the fourth joint surface 76a. A further, namely, the third wedge surface of the joint element 28a forms a fifth joint surface 80a which has two joint surface regions 82a and 84a that are inclined relative to each other. The fourth joint surface 76a of the prosthesis component 20a is inclined in the medial direction, the fifth joint surface 80a in the lateral direction. The joint surface region 82a is inclined relative to the plane 62a and thus to a longitudinal axis 86a defined by the second vertebral body contacting element 26a to a greater extent than a joint plane defined by the guidance surface 64a. The joint surface region 84a is inclined with respect to the longitudinal axis 86a to a lesser extent than the joint plane. The angle of inclination 88a of the joint surface region 82a to the plane 62a amounts to about 50°, but it could also lie within a range of 40° to 60°. The angle of inclination 90a of the joint surface region 84a with respect to the plane 62a amounts to circa 20°, although it could also lie within a range of 10° to 30°.

The lines of intersection of the joint surface region planes defined by the joint surface regions 82a and 84a run in the anterior-posterior direction, as does a line of intersection for the joint surface region plane defined by the joint surface region 84a and the plane defined by the fourth joint surface 76a. Furthermore, the joint element 28a comprises a stop surface 92a which runs substantially parallel to the plane 62a and which together with the joint surface region 62a defines a common line of intersection that runs in the anterior-posterior direction. The stop surface 92a cooperates with the projection 42a and can come into contact therewith during a corresponding relative movement of the joint element 28a and the first vertebral body contacting element 24a.

Figure 7A:
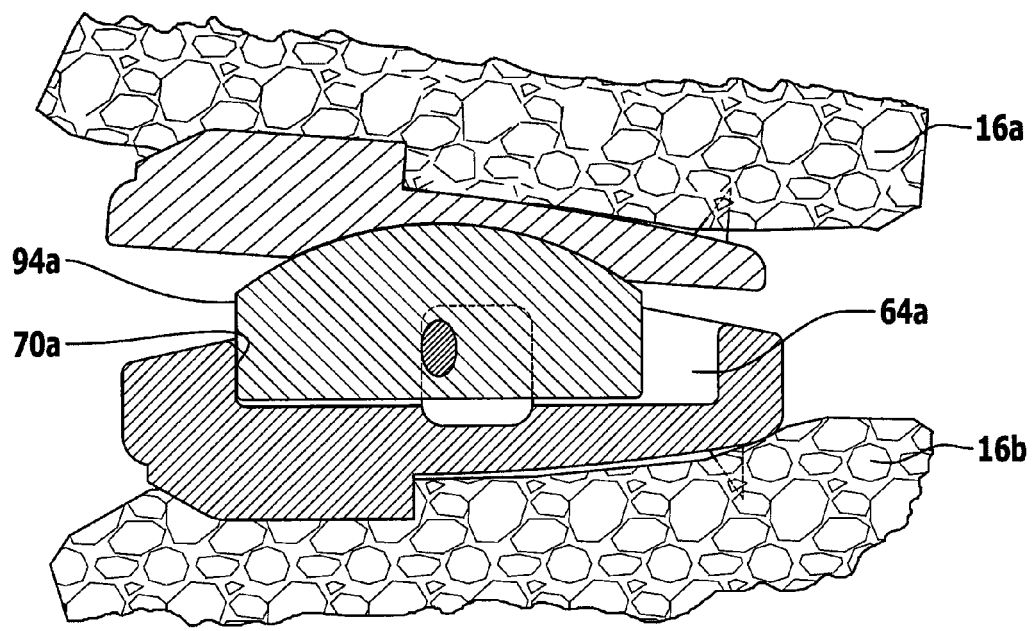
FIG. 7A: a sectional view analogous to FIG. 6 in an extension position.

Furthermore, the joint element 28a comprises substantially triangular end faces 94a which point in the anterior and posterior direction and run substantially parallel to the end faces 76a. The distance between the end faces 94a is somewhat shorter than the spacing between the end faces 70a, whereby a translatory movement of the joint element 28a in the seating 68a is possible in the anterior or posterior direction until the end faces 94a strike the respective end faces 70a, such as is illustrated in FIG. 7A for example.

Furthermore, the intervertebral disk prosthesis system 10 comprises a re-setting device 96 for returning the two ball joints 32a and 32b of the prosthesis components 20a and 20b back into the basic position from a position into which they were deflected from the basic position. The basic position of the intervertebral disk prosthesis system 10 is illustrated in FIG. 4 for example. The two prosthesis components 20a and 20b are formed such as to be mirror-symmetrical with respect to the medial plane 22 which defines a plane of symmetry in the basic position. The re-setting device 96 comprises two resetting members 98a and 98b which are substantially cuboidal and which are inserted into the seatings 68a, 68b in such a manner that they partially fill them. In particular, the side faces of the resetting member 98a rest flatly against the end faces 70a, the side face 72a as well as the bottom surface 74a. Furthermore, the resetting member 98a is formed in such a manner that it rests flatly against the fifth joint surface 80a, namely, by virtue of its correspondingly inclined resetting member surface regions 100a and 102a, whereby, in the basic position, the resetting member surface region 100a rests on the joint surface region 82a and the resetting member surface region 102a rests on the joint surface region 84a. An upper surface 104a of the resetting member 98a runs parallel to a lower surface 106a resting on the bottom surface 74a. Moreover, the resetting member 98a is provided at the anterior and posterior ends thereof with flattened portions 108a which are inclined by about 10° with respect to the upper surface 104 and extend in the direction of the anterior and posterior end faces 110a of the resetting member 98a and which, in particular, form additional stop surfaces for the joint element 28a during flexion/extension. The end faces 110a rest flatly against the end faces 70a. Preferably, the resetting member 98a is connected inseparably to the second vertebral body contacting element.

The resetting member 98a is formed from at least one resilient spring-like spring element which is preferably made of an elastomer. However, it could also consist of one or more coil springs or be a hydrogel element having the shape described above. Corresponding, not-illustrated hydraulic cylinders are also conceivable. At the same time, the re-setting device 96 also performs the function of a damping device. If the joint element 28a is pressed against the resetting member 98a, the resetting member 98 is resiliently deformed and is forced back into the seating 68a in a direction in which the influencing force is substantially directed.

The movement limiting device 30a comprises first and second stop members 112a and 114a. The first stop member 112a is in the form of a cylindrical stop pin 116a which is inserted into a blind hole 118a that is formed in the joint element 28a and is perpendicular relative to the fourth joint surface 76a, said stop pin protruding from the fourth joint surface 76a to the same extent as the depth of a cuboidal recess 120a defining the first stop member 112a. A free end 122a of the stop pin 116a is in the form of a hemisphere. The inner edges 124a of the recess 120a are rounded in correspondence with the radius of the free end 122. The cross section of the recess 120a defines a substantially rectangular surface region 126a in the guidance surface 64a. The length and breadth of the surface region 126a are greater than the diameter of the stop pin 116a so that the joint element 128a can be moved on the guidance surface 64a in both a translatory and rotary manner, in particular, about a longitudinal axis defined by the stop pin 116a insofar as such movement is permitted by the movement limiting device 30. Limitation of the movement is effected by the stop pin 116a striking the side faces of the recess 120a. In this way, movement of the joint element 28a can be limited in a defined manner in both the posterior and the anterior direction as well as in the direction of the resetting member 98a and away therefrom. The cross section of the first stop member 112a is greater than the cross section of the second stop member 114a. In consequence, the second stop member 114a is freely moveable within the surface region 126a.

The mode of functioning of the intervertebral disk prosthesis system 10 will now be described in more detail hereinafter in conjunction with FIGS. 1 to 8B.

Figure 8A:
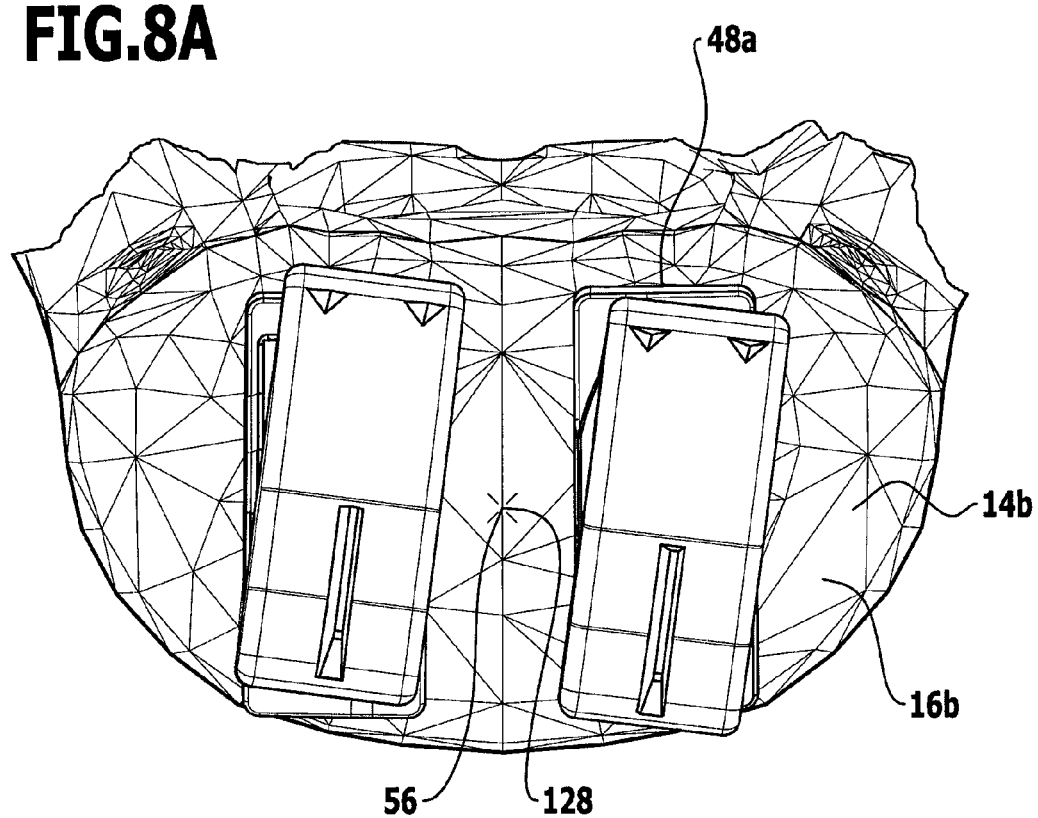
FIG. 8A: a plan view of the intervertebral disk prosthesis system from above in the case of an axial rotation about a longitudinal axis of the spinal column.
Figure 8B:
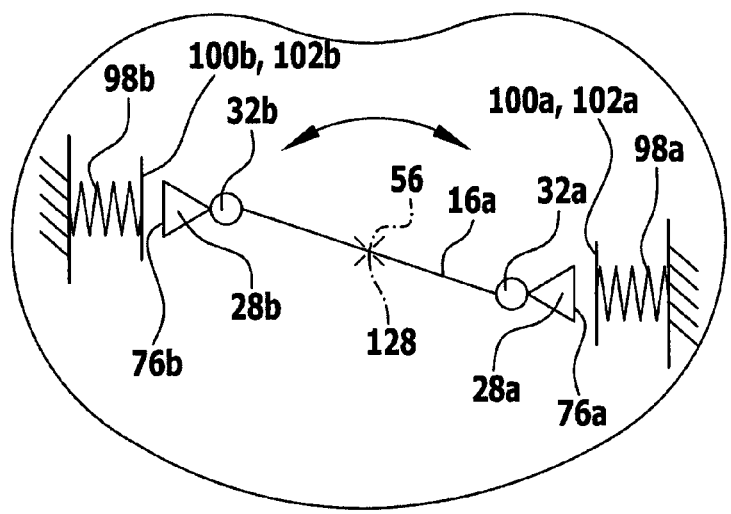
FIG. 8B: a schematic sketch depicting the principles involved in the case of a deflection of the intervertebral disk prosthesis system illustrated in FIG. 8A.

The two prosthesis components 20a and 20b are implanted between the laminas from the posterior via a bilateral point of entry, i.e. through an interlaminate point of entry. Preferably, they are inserted in parallel with each other in the anterior-posterior direction as is illustrated in FIGS. 1 and 8A. Overall, the intervertebral disk prosthesis system 10 is formed in such a manner that the position of the center of rotation 56 in the spatial region 58 is changeable in a defined manner in dependence on a deflection of the intervertebral disk prosthesis system from the basic position in which it is configured symmetrically.

In the broadest sense, the two prosthesis components 20a and 20b form two mutually independently working functional units which can each be inserted as a unit into the intervertebral disk space 12 by means of a suitable instrument, wherein the intervertebral disk space 12 is adapted to be spread apart by a unit. The two ball joints 32a and 32b do not have a common fulcrum. The first and second joint surfaces 34a, 34b and also 36a and 36b form flatly sliding pairs having a large area of contact due to the mutually corresponding radii of curvature. A further sliding pair is formed between the third and fourth joint surfaces 78a, 78b and 76a, 76b. In the first place, due to the angle of inclination 66a, 66b, the guidance surface 64a, 64b enables the joint element 28a, 28b to move in the anterior or the posterior direction in the case of an axial moment taken with respect to a longitudinal axis 128 which is defined by a segment of the spinal column that is itself defined by the vertebral bodies 16a and 16b as well as the intervertebral disk prosthesis system 10. Consequently, in combination with a rotation in the ball joints 32a and 32b, a superimposed axial rotational movement of the intervertebral disk prosthesis system 10 about the longitudinal axis 128 extending perpendicularly to the connecting line 60 can be achieved. A corresponding deflection of the ball joints 32a and 32b can be perceived in the plan view illustrated in FIG. 8A. The principle of the axial rotation is schematically illustrated in the sketch in FIG. 8B.

A flexion or an extension can also be achieved by means of the intervertebral disk prosthesis system 10, namely, by rotation about the connecting line 60 between the central points 38a and 38b. A limitation on the axial rotational movement is effected on the one hand by the mutually striking end faces 70a, 70b and 94a, 94b. On the other hand, the movement limiting device 30 together with the stop members 112a, 112b and 114a, 114b also provides a limitation on the movement of the joint elements 28a, 28b in the anterior and the posterior direction.

Figure 5A:
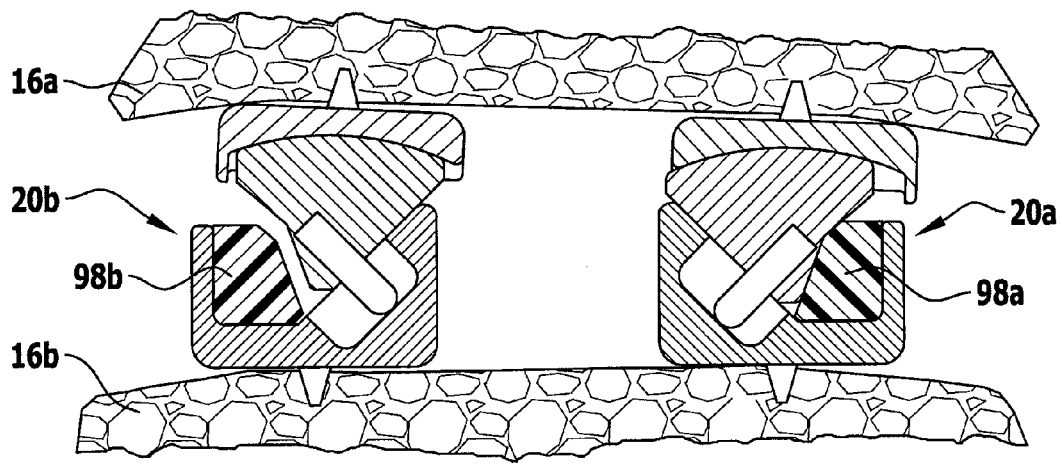
FIG. 5A: a sectional view analogous to FIG. 4 in the case of a right-hand side bending of the spinal column segment.
Figure 5B:
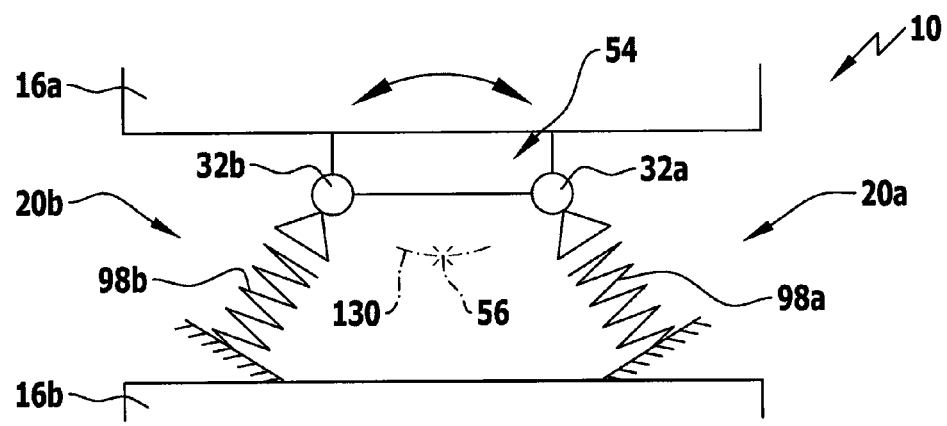
FIG. 5B: a schematic sketch depicting the principle of the structure of the intervertebral disk prosthesis system in a side or sectional view analogous to FIG. 4.

Furthermore, the intervertebral disk prosthesis system 10 also makes it possible to have a lateral rotational movement about the center of rotation 56, i.e. transverse to the anterior-posterior direction. The joint element 28a is pressed in the direction of the resetting member 98a by the corresponding introduction of a moment and consequently the first vertebral body contacting element 24a is displaced laterally and, at the same time, is guided by the guidance surface 64a in the direction of the second vertebral body contacting element 26a. Since an obligatory condition for the intervertebral disk prosthesis system 10 is that the first and second joint surfaces 34a, 34b and 36a, 36b should fit flatly together independently of any deflection of the intervertebral disk prosthesis system 10 from the basic position, the joint element 28b simultaneously slides on the guidance surface 64b during the lateral rotation described above so that the ball joint 32b moves in the direction of the prosthesis component 20a. Thereby, the joint element 28b rises somewhat from the resetting member 98b. In the event of a lateral rotation, a damping process always takes place by means of that particular resetting member to which a greater amount of pressure is applied. Limitation of the axial rotation is effected by means of the ball joint stop device 40 or by means of the movement limiting device 30. An example of a lateral rotational deflection is illustrated in FIG. 5a, the schematic sketch of FIG. 5B shows the principle of such a lateral rotational deflection.

Furthermore, it should be noted that, depending upon the angle of inclination 66a, 66b, the center of rotation 56 can migrate along a trajectory 130 in dependence on the degree of the deflection from the basic position. In consequence, in the exemplary embodiment illustrated in the Figures, the center of rotation 56 departs from the central plane in the basic position or the median plane 22 with increasing deflection of the intervertebral disk prosthesis system 10 from the basic position.

Figure 7B:
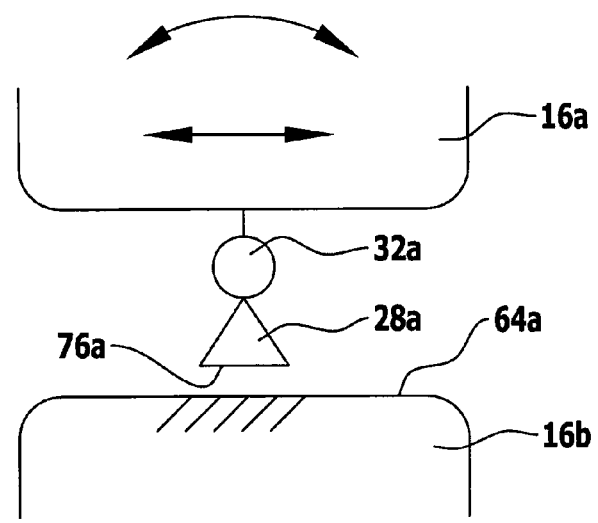
FIG. 7B: a schematic sketch depicting the principle of the intervertebral disk prosthesis system in accord with the sectional view depicted in FIG. 6.

In the event of a flexion/extension of the spinal column segment, there is an overall rotation of the intervertebral disk prosthesis system 10 about a rotational axis defined by the connecting line 60. Additionally however, due to the effective moments, a common translatory movement of the joint elements 28a, 28b can also take place in the anterior or posterior direction. In the first place, a movement of the joint elements 28a, 28b relative to the second vertebral body contacting elements 26a, 26b is limited by the end faces 70a, 70b and 94a, 94b as well as the stop members 112a, 112b and 114a, 114b of the movement limiting device 30. A schematic sketch depicting the principle of the extension/flexion movement is illustrated in FIG. 7B. Due to the construction of the intervertebral disk prosthesis system 10, a flexion/extension always causes a rotational and a translatory movement of the first and second vertebral body contacting elements 24a, 24b and 26a, 26b relative to each other.

Self evidently, the intervertebral disk prosthesis system 10 also enables axial rotational movements to be superimposed on the flexion/extension movements. In the case of such a movement too, the center of rotation 56 migrates along a defined trajectory 130 in dependence on the deflection of the intervertebral disk prosthesis system 10 from the basic position. In contrast to the known intervertebral disk prosthesis systems, physiologically coupled movements and in particular the above described flexion/extension movements having an axial rotational movement superimposed thereon are possible with the intervertebral disk prosthesis system 10 described above.

Due to the arrangement of the prosthesis components 20a, 20b, the functioning of the intervertebral disk prosthesis system 10 is substantially independent of the position of the prosthesis components 20a and 20b after the implantation process. The movement limiting device 30 as well as the ball joint stop device 40 limit any movement of the neighboring vertebral bodies 16a and 16b within the physiological boundaries. The re-setting device 96 ensures the requisite damping in the event of a movement of the vertebral bodies 16a, 16b relative to each other.

The vertebral body contacting elements 24a, 24b, 26a and 26b can be formed, in particular, from polyetheretherketone (PEEK), cobalt chrome, implant steel, titanium or a ceramic. In particular, provision may be made for the joint surfaces 34a, 34b, 36a, 36b, 78a, 78b, 76a, 76b and 80a, 80b to have a ceramic coating for the purposes of reducing friction and increasing abrasion resistance. The joint parts 28a, 28b can, in particular, be made from polyetheretherketone (PEEK), cobalt chrome, implant steel, titanium, ceramic, polyethylene (PE), silicone, hydrogel, polytetrafluorethylene (PTFE) or polyethylene terephthalate (PET) and they may optionally be provided with a ceramic coating when so desired.

The resetting members 98a, 98b prevent the joint parts 28a, 28b from moving downwardly along the guidance surface 64a, 64b onto the vertebral body contacting elements 26a, 26b upon impact, this being something that would normally occur due to a compressive force that is normally effective on an intervertebral disk. In dependence on the effective forces, the re-setting device 96 frequently serves less as a re-setting device, but rathermore, as a damping device for the intervertebral disk prosthesis system 10.

Due to the wedge-shaped arrangement of the joint elements 28a, 28b, the position of the center of rotation 56 moves along a defined trajectory 130 in the space, this being something that corresponds to a simulation of the physiological limitation of the movement by the facet joints of the vertebrae. The re-setting device 96 enables force-dependent kinetics of the intervertebral disk prosthesis system 10 by seeking to move the joint elements 28a, 28b accordingly back into the basic position.

Possible alternative constructions of the intervertebral disk prosthesis system are schematically illustrated in principle in FIGS. 9A to 12B.

Figure 9A:
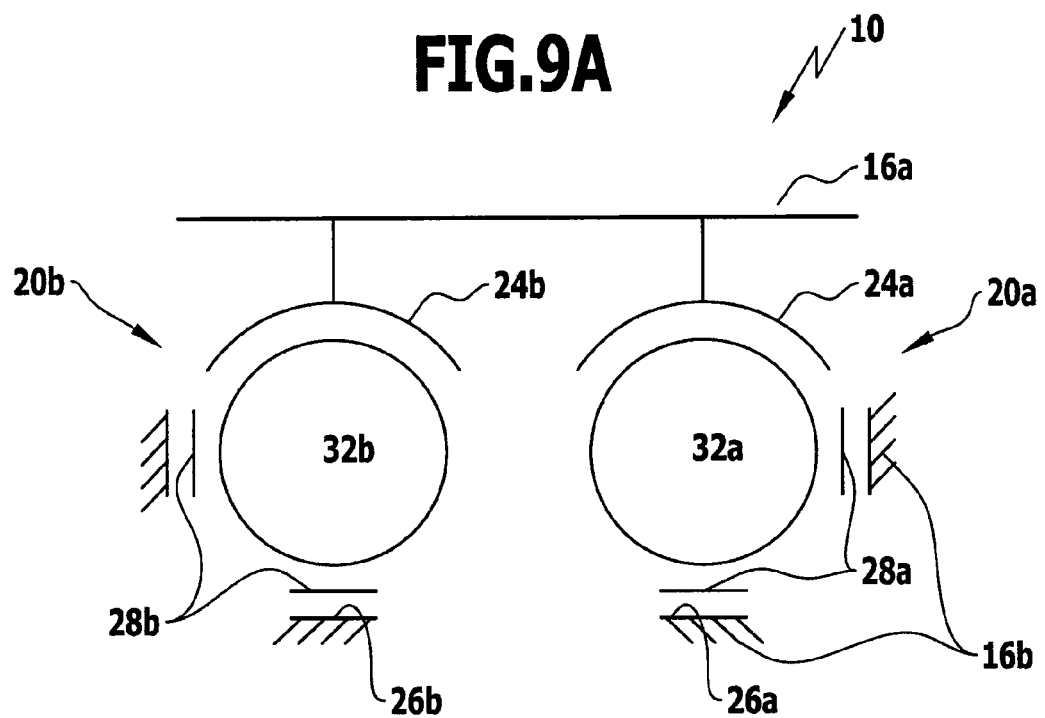
FIG. 9A: an illustration depicting the principle of a further embodiment of an intervertebral disk prosthesis system in a view from the front (in the anterior-posterior direction)
Figure 9B:
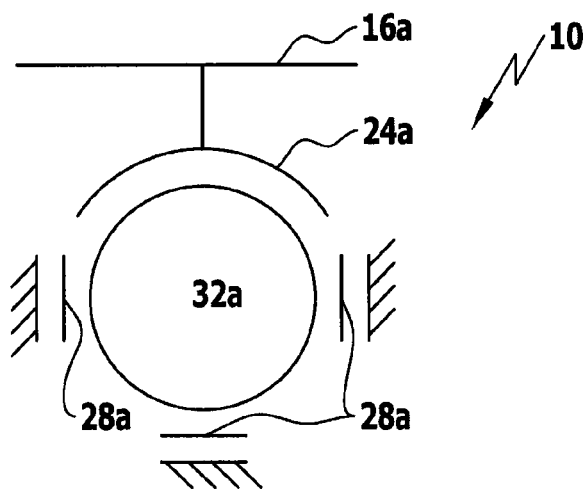
FIG. 9B: a schematic side view of the intervertebral disk prosthesis system depicted in FIG. 9A from the lateral side.
Figure 11A:
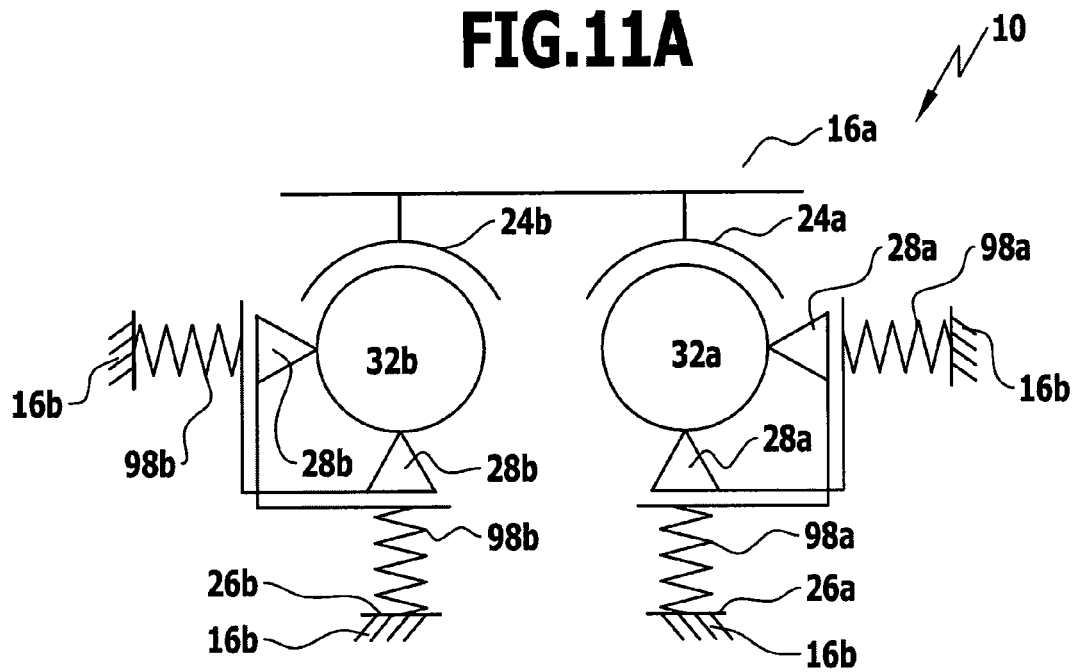
FIG. 11A: a sketch analogous to FIG. 9A depicting the principle of a further embodiment of an intervertebral disk prosthesis system.
Figure 11B:
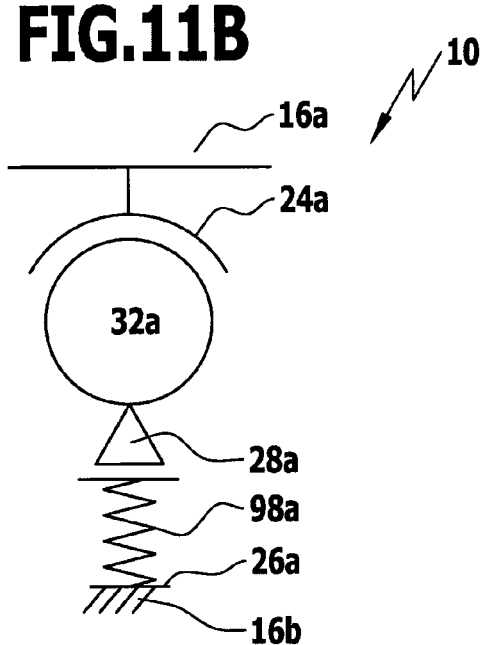
FIG. 11B: a sketch analogous to FIG. 9B depicting the principle of the intervertebral disk prosthesis system illustrated in FIG. 11A.
Figure 12A:
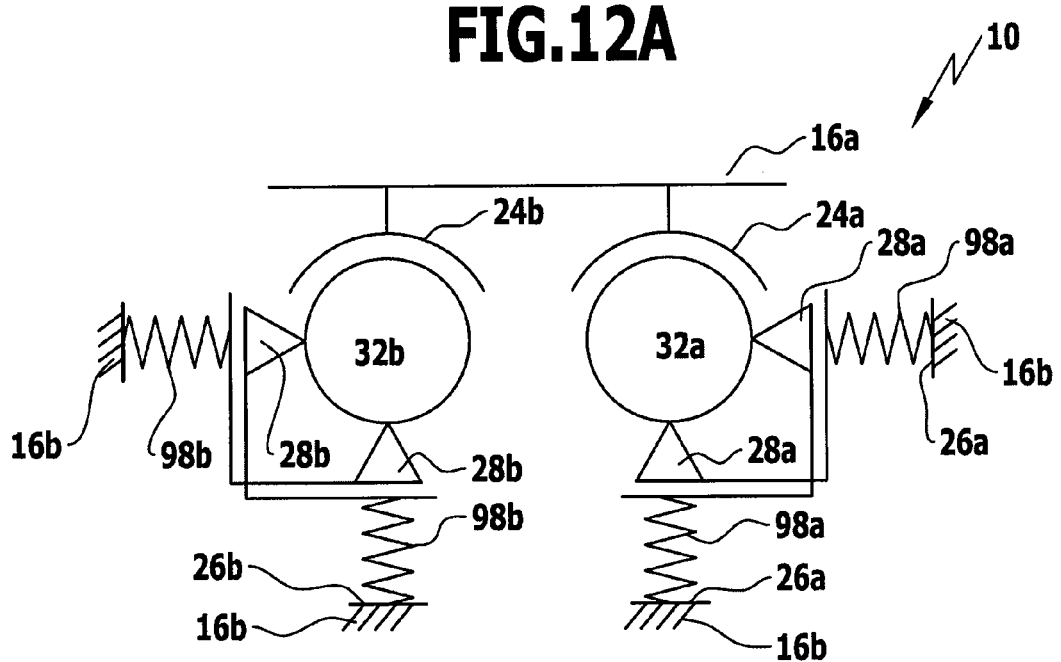
FIG. 12A: a sketch analogous to FIG. 9A depicting the principle of a further exemplary embodiment of an intervertebral disk prosthesis system.
Figure 12B:
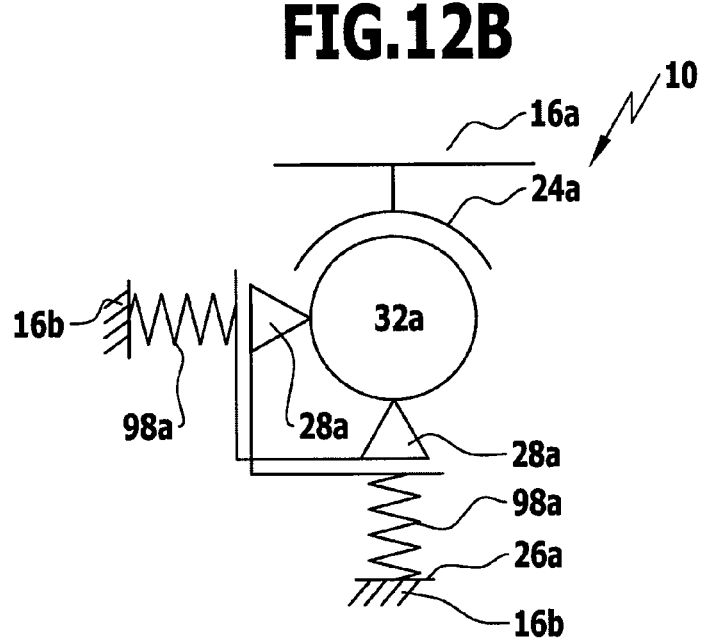
FIG. 12B: a sketch analogous to FIG. 9B depicting the principle of the intervertebral disk prosthesis system illustrated in FIG. 12A.

In FIGS. 9A and 9B, it is schematically illustrated how an intervertebral disk prosthesis system 10 incorporating ball joints 32a and 32b could also be formed in a corresponding manner by the provision of an appropriate sliding bearing for one or more joint elements 28a and 28b relative to the second vertebral body contacting elements 26a and 26b.

Optionally, in the case of the intervertebral disk prosthesis system 10 illustrated in FIGS. 10A and 10B which is formed without a re-setting device 96, one or more resetting members 98a, 98b, which damp any movement of the vertebral bodies 16a and 16b relative to each other, could additionally be inserted between the two vertebral body contacting element 26a and 26b.

In contrast to the intervertebral disk prosthesis system 10 illustrated in FIGS. 9A to 10B, specific support for the ball joints 32a and 32b in the intervertebral disk prosthesis systems 10 illustrated in FIGS. 11A to 12B is effected by appropriately cross-coupling the joint elements 28a and 28b to the vertebral body contacting elements 26a, 26b. Due to each of the two sliding pairs that together form the joint part elements 28a and 28b, superimposed movements in two linearly mutually independent directions can also be achieved and they can be damped by appropriate resetting members 98a, 98b.

The difference between the intervertebral disk prosthesis systems 10 such as are illustrated in FIGS. 11A, 11B and 12A, 12B lies in the construction of the re-setting device 96. In the case of the intervertebral disk prosthesis systems 10 illustrated in FIGS. 11A, 11B, damping only takes place as a consequence of a compression in the direction of the longitudinal axis 128, but in the case of the intervertebral disk prosthesis systems illustrated in FIGS. 12A, 12B there is also damping in the event of a movement of the ball element 32a, 32b in the anterior direction.

The illustrated schematic variants of intervertebral disk prosthesis systems are purely exemplary. In each case, it is crucial for all the intervertebral disk prosthesis systems that there be formed two mutually independent prosthesis components 20a and 20b which, when they are implanted between two vertebral bodies 16a and 16b, can define a common center of rotation or at least a common turning or rotational axis. To this end, the ball joints 32a, 32b can, in the described and illustrated way, be matched to one another in the required manner in regard to their relative movements by appropriate joint elements 28a, 28b and optionally by the employment of re-setting devices 96 in order, in particular, to define a common center of rotation 56 in such a manner that the sliding pairs defining the ball joints 32a, 32b always fit flatly together.

The invention claimed is:

1. An intervertebral disk prosthesis system for forming an artificial intervertebral disk comprising a first prosthesis component and a second prosthesis component which is independent of the first prosthesis component, wherein each of the two prosthesis components comprises a first and a second vertebral body contacting element for placement on neighboring vertebral bodies which bound an intervertebral disk space of a spinal column and a joint element that is mounted between and is moveable relative to at least one of the first and second vertebral body contacting elements, wherein each prosthesis component comprises a ball joint that is mounted in a moveable manner between the first and second vertebral body contacting elements,
the intervertebral disk prosthesis system further comprising a guidance device for defining a superior swivel joint that is defined by both prosthesis components together for simultaneously twisting the two first vertebral body contacting elements relative to the two second vertebral body contacting elements about a common center of rotation which is located in a spatial region between central points of the two ball joints,
the guidance device on each prosthesis component comprising a respective guidance surface for guiding a movement of the two ball joints relative to the second vertebral body contacting element, the guidance surface defining a joint plane that is inclined at an angle of inclination relative to a longitudinal axis which is oriented in the direction of the first vertebral body contacting element in a basic position and is defined by the second vertebral body contacting element, the angle of inclination of the joint plane having a value within a range of 10° to 80°.

2. The intervertebral disk prosthesis system in accordance with claim 1, wherein the first vertebral body contacting element and the associated joint element define the respective ball joint.

3. The intervertebral disk prosthesis system in accordance with claim 1, wherein the spatial region is bounded by two planes extending perpendicularly relative to a connecting line between the central points of the two ball joints.

4. The intervertebral disk prosthesis system in accordance with claim 1, wherein the intervertebral disk prosthesis system is formed in such a manner that the position of the center of rotation in the spatial region is changeable in a defined way in dependence on the deflection of the intervertebral disk prosthesis system from the basic position in which it is symmetrically configured.

5. The intervertebral disk prosthesis system in accordance with claim 1, the intervertebral disk prosthesis system defining a basic-position central plane between the central points, said plane being oriented perpendicularly relative to the connecting line, and the center of rotation being located thereupon in the basic position.

6. The intervertebral disk prosthesis system in accordance with claim 4, wherein the intervertebral disk prosthesis system is formed in such a manner that the spacing of the center of rotation from the basic position central plane increases with increasing deflection of the intervertebral disk prosthesis system from the basic position.

7. The intervertebral disk prosthesis system in accordance with claim 4, wherein the intervertebral disk prosthesis system is formed in such a manner that the center of rotation is located on the basic position central plane independently of any deflection of the intervertebral disk prosthesis system from the basic position.

8. The intervertebral disk prosthesis system in accordance with claim 1 wherein a connecting line between the central points of the two ball joints defines a flexion/extension axis of the intervertebral disk prosthesis system.

9. The intervertebral disk prosthesis system in accordance with claim 1, wherein a radius of the ball joints is greater than the spacing of the two central points of the ball joints from each other.

10. The intervertebral disk prosthesis system in accordance with claim 1, wherein the first and the second prosthesis components are formed such as to be mutually mirror-symmetrical in the basic position taken with respect to a plane of symmetry running therebetween.

11. The intervertebral disk prosthesis system in accordance with claim 10, wherein the connecting line in the basic position defines a common rotational axis of the intervertebral disk prosthesis system which extends in a lateral direction transverse to the plane of symmetry.

12. The intervertebral disk prosthesis system in accordance with claim 10, wherein the plane of symmetry extends in an anterior-posterior direction of the intervertebral disk prosthesis system.

13. The intervertebral disk prosthesis system in accordance with claim 10, wherein the longitudinal axes of the two prosthesis components are inclined with respect to the plane of symmetry or extend in parallel therewith.

14. The intervertebral disk prosthesis system in accordance with claim 10, said intervertebral disk prosthesis system defining an axial rotational axis which includes the center of rotation and which, at least in a non-deflected basic position, extends in the plane of symmetry or is parallel thereto and extends perpendicularly or substantially perpendicularly relative to contact surfaces defined by the first and second vertebral body contacting elements.

15. The intervertebral disk prosthesis system in accordance with claim 1, wherein the first vertebral body contacting element defines a first joint surface, the joint element defines a second joint surface which is formed in correspondence with the first joint surface, the second joint surface forms a part of a spherical surface and the first joint surface forms a part of a hollow ball surface.

16. The intervertebral disk prosthesis system in accordance with claim 1, wherein the guidance surface is formed for guiding a movement of the respective joint element relative to the second vertebral body contacting element.

17. The intervertebral disk prosthesis system in accordance with claim 16, wherein the guidance surface is formed on at least one of the joint element and the second vertebral body contacting element.

18. The intervertebral disk prosthesis system in accordance with claim 15, wherein the second vertebral body contacting element defines a third joint surface and the joint element defines a fourth joint surface which is formed in correspondence with the third joint surface, and the third or the fourth joint surface forms the guidance surface.

19. The intervertebral disk prosthesis system in accordance with claim 1, wherein the joint element is at least one of displaceable relative to the second vertebral body contacting element in parallel with the joint plane and can be rotated about an axis of rotation running perpendicularly relative to the joint plane.

20. The intervertebral disk prosthesis system in accordance with claim 1, wherein the angle of inclination has a value within a range of about 30° to about 60°.

21. The intervertebral disk prosthesis system in accordance with claim 1, wherein the angle of inclination amounts to about 45°.

22. The intervertebral disk prosthesis system in accordance with claim 18, wherein the third joint surface is oriented in a lateral direction and in the direction of the first vertebral body contacting element.

23. The intervertebral disk prosthesis system in accordance with claim 1, wherein a movement limiting device is provided for limiting any relative movement of the joint element and the second vertebral body contacting element of the respective prosthesis component relative to each other.

24. The intervertebral disk prosthesis system in accordance with claim 23, wherein the movement limiting device comprises a first and a second stop member, in that the joint element comprises the one of the stop members and the second vertebral body contacting element comprises the other one of the two stop members, the first stop member defines a surface region of the joint plane, and the second stop member is freely moveable within the surface region.

25. The intervertebral disk prosthesis system in accordance with claim 24, wherein the surface region is rectangular or substantially rectangular.

26. The intervertebral disk prosthesis system in accordance with claim 24, wherein a cross section of the first stop member parallel to the joint plane is larger than a cross section of the second stop member parallel to the joint plane.

27. The intervertebral disk prosthesis system in accordance with claim 24, wherein the second stop element is oriented perpendicularly or substantially perpendicularly relative to the joint plane.

28. The intervertebral disk prosthesis system in accordance with claim 24, wherein the first stop member is in the form of a recess and the second stop member is in the form of a projection extending into the recess.

29. The intervertebral disk prosthesis system in accordance with claim 28, wherein the projection is in the form of a stop pin.

30. The intervertebral disk prosthesis system in accordance with claim 28, wherein the projection has a circular cross section.

31. The intervertebral disk prosthesis system in accordance with claim 28, wherein a free end of the projection is in the form of a hemisphere.

32. The intervertebral disk prosthesis system in accordance with claim 28, wherein the inner edges of the recess are rounded in correspondence with at least one of the cross section and the shape of a free end of the projection.

33. The intervertebral disk prosthesis system in accordance with claim 24, wherein the joint element comprises the second stop member.

34. The intervertebral disk prosthesis system in accordance with claim 24, wherein the joint element and the second stop member are in two-piece form and are non-detachably connected to one another.

35. The intervertebral disk prosthesis system in accordance with claim 18, wherein the joint element defines a fifth joint surface and the fifth joint surface rests directly or indirectly against the second vertebral body contacting element.

36. The intervertebral disk prosthesis system in accordance with claim 35, wherein the fifth joint surface is inclined relative to the fourth joint surface.

37. The intervertebral disk prosthesis system in accordance with claim 35, wherein a line of intersection of the planes defined by the fourth and fifth joint surfaces runs in an anterior-posterior direction.

38. The intervertebral disk prosthesis system in accordance with claim 35, wherein the fourth joint surface is inclined in the medial direction and the fifth joint surface is inclined in a lateral direction.

39. The intervertebral disk prosthesis system in accordance with claim 35, wherein the fifth joint surface has two joint surface regions which are inclined relative to each other and which define joint surface region planes that are inclined relative to each other.

40. The intervertebral disk prosthesis system in accordance with claim 39, wherein the one of the joint surface regions is inclined relative to a longitudinal axis defined by the second vertebral body contacting element to a greater extent than the joint plane, and the other one of the joint surface regions is inclined relative to the longitudinal axis to a lesser extent than the joint plane.

41. The intervertebral disk prosthesis system in accordance with claim 40, wherein an angle of inclination of the one joint surface region relative to the longitudinal axis lies within a range of about 40° to about 60°, and an angle of inclination of the other joint surface region relative to the longitudinal axis lies in a range of about 10° to about 30°.

42. The intervertebral disk prosthesis system in accordance with claim 39, wherein a line of intersection of the joint surface region planes extends in an anterior-posterior direction.

43. The intervertebral disk prosthesis system in accordance with claim 24, further comprising a re-setting device for returning the two ball joints of the prosthesis components back into the basic position from a position into which the joint has been deflected from the basic position.

44. The intervertebral disk prosthesis system in accordance with claim 43, wherein the re-setting device is formed in such a manner that, in the basic position of the intervertebral disk prosthesis system, the second stop member is spaced from lateral boundary surfaces of the first stop element which defines the surface region.

45. The intervertebral disk prosthesis system in accordance with claim 43, wherein the re-setting device is formed in such a manner that, in a basic position of the intervertebral disk prosthesis system, the joint element, without biasing the re-setting device, is in contact therewith.

46. The intervertebral disk prosthesis system in accordance with claim 43, wherein the joint element defines a fifth joint surface and the fifth joint surface rests directly or indirectly against the second vertebral body contacting element, and wherein the re-setting device engages with the fifth joint surface.

47. The intervertebral disk prosthesis system in accordance with claim 43, wherein the re-setting device is formed in such a manner that, in a basic position of the intervertebral disk prosthesis system, the second vertebral body contacting element, without biasing the re-setting device, is in contact therewith.

48. The intervertebral disk prosthesis system in accordance with claim 43, wherein the re-setting device is spring biased in the basic position.

49. The intervertebral disk prosthesis system in accordance with claim 43, wherein the joint element is movable from the basic position in the lateral direction against the effect of the re-setting device.

50. The intervertebral disk prosthesis system in accordance with claim 43, wherein the joint element is movable from the basic position in the direction of the second vertebral body contacting element against the effect of the re-setting device.

51. The intervertebral disk prosthesis system in accordance with claim 43, wherein the joint element is movable from the basic position in the anterior direction against the effect of the re-setting device.

52. The intervertebral disk prosthesis system in accordance with claim 43, wherein the joint element is movable from the basic position in the posterior direction against the effect of the re-setting device.

53. The intervertebral disk prosthesis system in accordance with claim 43, wherein the re-setting device comprises at least one resetting member which engages with the joint element and with the second vertebral body contacting element.

54. The intervertebral disk prosthesis system in accordance with claim 53, wherein the re-setting device comprises two resetting members which define directions of force that are linearly mutually independent.

55. The intervertebral disk prosthesis system in accordance with claim 53, wherein the re-setting device comprises a single resetting member.

56. The intervertebral disk prosthesis system in accordance with claim 53, wherein the joint element defines a fifth joint surface and wherein the at least one resetting member has a joint element contact surface which rests on the fifth joint surface in the basic position.

57. The intervertebral disk prosthesis system in accordance with claim 56, wherein the joint element contact surface comprises two joint element contact surface sections which define joint element contact surface planes that are inclined relative to each other.

58. The intervertebral disk prosthesis system in accordance with claim 57, wherein the fifth joint surface rests directly or indirectly against the second vertebral body contacting element, wherein the fifth joint surface has two joint surface regions which are inclined relative to each other and which define joint surface region planes that are inclined relative to each other and wherein the joint element contact surface planes extend parallel to the joint surface region planes.

59. The intervertebral disk prosthesis system in accordance with claim 57, wherein the joint element contact surface planes coincide with the joint surface region planes in the basic position.

60. The intervertebral disk prosthesis system in accordance with claim 1, wherein the joint element is made of polyetheretherketone (PEEK), cobalt chrome, implant steel, titanium, a ceramic, polyethylene, silicone, hydrogel, polytetrafluoroethylene (PTFE) or polyethylene terephthlate (PET).

61. The intervertebral disk prosthesis system in accordance with claim 1, wherein the first and/or the second vertebral body contacting element are made of at least one of polyetheretherketone (PEEK), cobalt chrome, implant steel, titanium and a ceramic.

62. The intervertebral disk prosthesis system in accordance with claim 35, wherein at least one of the first and the second and the third and the fourth and the fifth joint surface are provided with a ceramic coating.

63. The intervertebral disk prosthesis system in accordance with claim 53, wherein the resetting member is formed from at least one resiliently-formed spring element.

64. The intervertebral disk prosthesis system in accordance with claim 63, wherein the at least one resiliently-formed spring element is formed from an elastomer or is in the form of a coil spring, a hydrogel element or a hydraulic cylinder.

65. The intervertebral disk prosthesis system in accordance with claim 53, wherein the joint element forms or comprises the resetting member.

66. The intervertebral disk prosthesis system in accordance with claim 1, wherein at least one of the vertebral body contacting elements comprises at least one anchoring element for anchoring the at least one vertebral body contacting element to a vertebral body.

67. The intervertebral disk prosthesis system in accordance with claim 66, wherein the at least one anchoring element is in the form of a projection.

68. The intervertebral disk prosthesis system in accordance with claim 67, wherein the projection is wedge shaped or pointed.

69. The intervertebral disk prosthesis system in accordance with claim 66, wherein the at least one anchoring element is formed in one-piece manner with the at least one vertebral body contacting element.

70. The intervertebral disk prosthesis system in accordance with claim 66, wherein the at least one anchoring element is in the form of a separate component that is connectable to the at least one vertebral body contacting element.

71. The intervertebral disk prosthesis system in accordance with claim 66, wherein the at least one anchoring element is in the form of a screw or a clamp.

72. The intervertebral disk prosthesis system in accordance with claim 1, further comprising a ball joint stop device for limiting any relative motion of the joint elements and the associated first vertebral body contacting elements relative to each other.

73. The intervertebral disk prosthesis system in accordance with claim 72, wherein the ball joint stop device comprises a projection which is formed on at least one of the joint element and on the first vertebral body contacting element.

74. The intervertebral disk prosthesis system in accordance with claim 73, wherein the projection is in each case arranged laterally at the side of the respective prosthesis component.

75. The intervertebral disk prosthesis system in accordance with claim 72, wherein the ball joint stop device is formed in one-piece manner with at least one of the respective joint elements and the respective first vertebral body contacting elements.

76. The intervertebral disk prosthesis system in accordance with claim 1, wherein each joint element is substantially wedge-shaped.

77. The intervertebral disk prosthesis system in accordance with claim 1, wherein the respective joint planes of the guidance surfaces facilitate lateral movement of the respective ball joints relative to the respective guidance surfaces.

\* \* \* \* \*

UNITED STATES PATENT AND TRADEMARK OFFICE
CERTIFICATE OF CORRECTION

PATENT NO. : 8,262,733 B2
APPLICATION NO. : 12/497132
DATED : September 11, 2012
INVENTOR(S) : Jens Beger and Alexander Haas It is certified that error appears in the above-identified patent and that said Letters Patent is hereby corrected as shown below:

At Column 22, line 8, "claim 1 wherein" should read -- claim 1, wherein --

At Column 25, line 49, "terephthlate" should read -- terephthalate --

Signed and Sealed this
Fifth Day of February, 2013

Teresa Stanek Rea
*Acting Director of the United States Patent and Trademark Office*